United States Patent
Rizzo

(10) Patent No.: US 9,560,987 B2
(45) Date of Patent: Feb. 7, 2017

(54) LOCALIZED PHYSIOLOGIC STATUS FROM LUMINOSITY AROUND FINGERTIP OR TOE

(75) Inventor: Nancy R. Rizzo, Scottsdale, AZ (US)

(73) Assignee: EPIC Research & Diagnostics, Inc., Scottsdale, AZ (US)

( * ) Notice: Subject to any disclaimer, the term of this patent is extended or adjusted under 35 U.S.C. 154(b) by 83 days.

(21) Appl. No.: 14/125,086

(22) PCT Filed: Aug. 15, 2012

(86) PCT No.: PCT/US2012/050956
§ 371 (c)(1),
(2), (4) Date: Jul. 18, 2014

(87) PCT Pub. No.: WO2013/025809
PCT Pub. Date: Feb. 21, 2013

(65) Prior Publication Data
US 2014/0350413 A1 Nov. 27, 2014

Related U.S. Application Data

(60) Provisional application No. 61/523,746, filed on Aug. 15, 2011.

(51) Int. Cl.
*A61B 5/00* (2006.01)
*A61B 5/053* (2006.01)
(Continued)

(52) U.S. Cl.
CPC .......... *A61B 5/0533* (2013.01); *A61B 5/0082* (2013.01); *A61B 5/0093* (2013.01); *A61B 5/02* (2013.01);
(Continued)

(58) Field of Classification Search
None
See application file for complete search history.

(56) References Cited

U.S. PATENT DOCUMENTS 3,877,790 A * 4/1975 Robinson ................ G02F 1/133
349/143
3,994,283 A 11/1976 Farley
(Continued)

FOREIGN PATENT DOCUMENTS

CN 1394299 1/2003
CN 101262813 9/2008
(Continued)

OTHER PUBLICATIONS

Dr. Korotkov, "Measuring Energy Fields. State of the Science", vol. 1.*

(Continued)

*Primary Examiner* — Tse Chen
*Assistant Examiner* — Joanne Hoffman
(74) *Attorney, Agent, or Firm* — Jennings Strouss & Salmon PLC; Michael K. Kelly

(57) ABSTRACT

Spatial light response around a fingertip or toe of a subject in response to electrical stimulation can be associated to a specified remote particular body anatomy, location, component, or system such as for providing a particularized physiological status indicator or other particularized response indication that is particular to the specified particular body anatomy, location, component, or system.

23 Claims, 6 Drawing Sheets

(51) Int. Cl.
*A61B 5/05* (2006.01)
*H04N 5/225* (2006.01)
*A61B 5/02* (2006.01)
*A61B 5/08* (2006.01)
*A61B 5/20* (2006.01)

(52) U.S. Cl.
CPC . *A61B 5/05* (2013.01); *A61B 5/08* (2013.01); *A61B 5/201* (2013.01); *A61B 5/42* (2013.01); *A61B 5/4842* (2013.01); *A61B 5/6825* (2013.01); *A61B 5/6826* (2013.01); *A61B 5/6829* (2013.01); *A61B 5/7275* (2013.01); *H04N 5/2256* (2013.01)

(56) References Cited

U.S. PATENT DOCUMENTS

| | | |
|---|---|---|
| 4,195,641 A | 4/1980 | Joines |
| 4,222,658 A | 9/1980 | Mandel |
| 4,386,834 A | 6/1983 | Toolan |
| 4,542,969 A | 9/1985 | Omura |
| 4,557,271 A | 12/1985 | Stoller |
| 4,679,924 A | 7/1987 | Wamsley |
| 4,746,213 A | 5/1988 | Knapp |
| 4,794,934 A | 1/1989 | Motoyama |
| 5,208,453 A | 5/1993 | Hostetler |
| 5,366,379 A | 11/1994 | Yang |
| 5,427,113 A | 6/1995 | Hiroshi |
| 5,779,483 A | 7/1998 | Cho |
| 6,016,450 A | 1/2000 | Crock |
| 6,099,473 A | 8/2000 | Liu |
| 6,392,249 B1* | 5/2002 | Struye ............ G01T 1/2012 250/484.4 |
| 6,466,688 B1 | 10/2002 | Ramstack |
| 6,678,398 B2 | 1/2004 | Wolters |
| 6,746,397 B2 | 6/2004 | Lee |
| 6,817,982 B2* | 11/2004 | Fritz ............ A61B 8/0858 382/128 |
| 7,076,293 B2 | 7/2006 | Wang |
| 7,110,582 B1 | 9/2006 | Hay |
| 7,156,866 B1 | 1/2007 | Riggs |
| 7,403,816 B2 | 7/2008 | Ohkura |
| 7,697,827 B2 | 4/2010 | Konicek |
| 7,869,636 B2 | 1/2011 | Korotkov |
| 7,942,816 B2 | 5/2011 | Satoh |
| 7,995,820 B2 | 8/2011 | de Barros Carneiro |
| 8,321,010 B2 | 11/2012 | Korotkov et al. |
| 8,423,118 B2 | 4/2013 | Wenzel |
| 8,488,863 B2 | 7/2013 | Boucheron |
| 8,582,831 B2 | 11/2013 | Miura |
| 8,611,620 B2 | 12/2013 | Karasikov |
| 8,666,475 B2 | 3/2014 | Hirsch |
| 8,781,191 B2 | 7/2014 | Lang |
| 8,787,633 B2 | 7/2014 | Robinson |
| 8,831,299 B2 | 9/2014 | Kurtz |
| 8,989,848 B2 | 3/2015 | Rorabaugh |
| 2002/0106041 A1* | 8/2002 | Chang ............ H04B 7/18515 375/347 |
| 2003/0016856 A1* | 1/2003 | Walker ............ G06T 1/00 382/132 |
| 2003/0095316 A1 | 5/2003 | Herbepin |
| 2004/0087838 A1 | 5/2004 | Galloway |
| 2005/0014998 A1* | 1/2005 | Korotkov ............ A61B 5/05 600/315 |
| 2006/0266371 A1 | 11/2006 | Vainshelboim |
| 2007/0127575 A1* | 6/2007 | Ho ............ H04N 19/56 375/240.16 |
| 2007/0242269 A1* | 10/2007 | Trainer ............ G01N 15/0205 356/336 |
| 2007/0285743 A1* | 12/2007 | Hirayama ............ H04N 1/6033 358/504 |
| 2008/0108909 A1 | 5/2008 | Reger |
| 2009/0018432 A1 | 1/2009 | He |
| 2009/0080608 A1* | 3/2009 | Vizard ............ G01N 23/087 378/54 |
| 2009/0209858 A1 | 8/2009 | Oelze |
| 2009/0326401 A1 | 12/2009 | Jonckheere |

FOREIGN PATENT DOCUMENTS

| | | |
|---|---|---|
| CN | 101605495 | 12/2009 |
| RU | 2143841 | 1/2000 |
| WO | 03071391 | 8/2003 |
| WO | WO 2008 114065 | 9/2008 |
| WO | 2011028146 | 3/2011 |

OTHER PUBLICATIONS

Rubik, "Digital High-Voltage Electrophotographic Measures of the Fingertips of Subjects Pre- and Post-Qigong", Evid Based Integrative Meds, 2(4), pp. 245-252, 2005.*
Dr. Korotkov, GDV Camera, http://gdvcamera.com/gdvcamera-bio-well/.*
Dr. Korotkov, GDV Software, http://www.gdvsoftware.com/gdv-software-of-the-world/.*
Kononenko, "Machine Learning for Medical Diagnosis: History, State of the Art and Perspective" (1998).
Kononenko, "Machine Learning and GDV Images: Diagnosis and Therapy Verification" In Proc. Biology and Cognitive Science, pp. 84-87. (1999) see http://km.fri.uni-lj.si/slobo99.doc.
Rubik, "Measurement of the Human Biofield and Other Energetic Instruments", Chapter 20 of Energetics and Splurituality by Lyn Freeman see http://www.faim.org/energymedicine/measurement-human-biofield.html (2009).
Konstantin G. Korotkov, et al., Analysis and Monitoring of Human Energy State with Gas Discharge Visualization Technique. Proceedings of the 18th IEEE Symposium on Computer-Based Medical Systems, U.S., IEEE, 2005, p. 431-436, http://ieeexplore.ieee.org.
Natarajan Meghanathan, et al., Clustering Model to Identify Biological Signatures for English Language Anxiety. Biomedical Sciences and Engineering Conference, U.S., IEEE, 2010, p. 1-4. http://ieeexplore.ieee.org.
Nataliya Kostyuk, et al., Autism From a Biometric Perspective, Int. J. Environ. Res. Public Health 2010, 7, 1984-1995.
Berney Williams, How Does Gas Discharge Visualization Technique Assess a Body? Emerging Models of Energy and Control in Biophysics and Physiology. Proceedings of the 18th IEEE Symposium on Computer-Based Systems. U.S., IEEE, 2005. p. 446-448. http://ieeexplore.ieee.org.
Sergey K. Savelyev, et al., The Automated Diagnostics of Person Psychophysical Condition on the Base of Gas-Discharge Visualization (GDV) Method, Second International Conference on Lasers for Measurements and Information Transfer, Proceedings of SPIE vol. 4680 (2002), p. 281-288.
Motoyama, Hiroshi; "How to Measure and Diagnose the Functions of Meridians and Corresponding Internal Organs"; 1975; pp. 81-164; The Institute for Religious Psychology, Tokyo, Japan.
Ivanov, Plamen; "Su Jok and Moxa"; 2002; entire electronic version; Mediks Ltd, Bulgaria.
Korotkov, Konstantin; "Aura and Consciousness: New Stage of Scientific Understanding"; 1999; pp. 58-71, 74-75, 84-89, 202-217; St Petersburg division of Russian Ministry of Culture, State Editing & Publishing Unit "Kultura", St. Petersburg, Russia.
Korotkov, Konstantin; "Human Energy Field: Study With GDV Bioelectrography"; 2002; pp. 10, 19; Backbone Publishing Co., Fair Lawn, New Jersey, USA.
Korotkov, Konstantin; "Human Energy Field: Study With GDV Bioelectrography"; 2002; pp. 266-269, 280-326; Backbone Publishing Co., Fair Lawn, New Jersey, USA.

* cited by examiner

ClearView Report
Epic Validation
Vist Date: Friday, April 09, 2010 at 11:00:42 AM

| | Normal Physical | | Out of Range Physical | | Out of Range Autonomic | | Normal Autonomic | | Notes |
|---|---|---|---|---|---|---|---|---|---|
| | Left | Right | Left | Right | Left | Right | Left | Right | |
| Sensory & Skeletal Systems | | | | | | | | | |
| Eye (L) | 12 | 0 | | | | | 12 | 0 | |
| Eye (R) | | | 16 | 16 | 16 | 16 | | | |
| Ear/Nose/Sinus (L) | | | 25 | 40 | 25 | 40 | | | |
| Ear/Nose/Sinus (R) | | | 25 | 27 | 48 | 27 | | | |
| Jaw/Teeth (L) | | | 14 | 27 | 14 | 27 | | | |
| Jaw/Teeth (R) | 0 | 6 | | | | | 0 | 6 | |
| Cervical Spine | 12 | 12 | | | | | 12 | 12 | |
| Thoracic Spine | 0 | 0 | | | | | 0 | 0 | |
| Lumbar Spine | 0 | 0 | | | | | 0 | 0 | |
| Sacrum | | | 0 | 40 | 0 | 40 | | | |
| Coccyx/Pelvis | 12 | 6 | | | | | 12 | 6 | |
| Nervous & Immune Systems | | | | | | | | | |
| Nervous System | | | 27 | 6 | 27 | 6 | | | |
| Hypothalamus | 4 | 0 | | | | | 4 | 0 | |
| Pituitary | 8 | 12 | | | | | 8 | 12 | |
| Pineal | | | 0 | 27 | 0 | 27 | | | |
| Cerebral Cortex | | | 18 | 10 | 18 | 10 | | | |
| Cerebral Vessels | | | 40 | 0 | 40 | 0 | | | |
| Immune System | | | 25 | 27 | 25 | 27 | | | |
| Spleen | 12 | 0 | | | | | 12 | 0 | |

*FIG. 5*

| Organ | Physical System | | Autonomic System | |
|---|---|---|---|---|
| | Left Hand | Right Hand | Left Hand | Right Hand |
| Cardiovascular Circulation | 16 | 0 | 16 | 0 |
| Coronary Vessels | 0 | 16 | 0 | 27 |
| Heart | 0 | 12 | 0 | 0 |
| Heart (Left Side) | 14 | 0 | 14 | 0 |
| Heart (Right Side) | 8 | 0 | 8 | 0 |
| Throat/Larynx/Trachea/Thyroid | 16 | 25 | 16 | 25 |
| Gallbladder | 0 | 16 | 0 | 16 |
| Liver | 6 | 14 | 0 | 14 |
| Pancreas | 12 | 25 | 12 | 45 |
| Thyroid | 4 | 0 | 4 | 0 |
| Appendix | 0 | 4 | 0 | 4 |
| Ascending Colon | 0 | 0 | 0 | 0 |
| Descending Colon | 12 | 0 | 27 | 0 |
| Rectum | 0 | 0 | 0 | 0 |
| Sigmoid Colon | 0 | 0 | 0 | 0 |
| Transverse Colon | 16 | 45 | 16 | 45 |
| Cerebral Cortex | 18 | 10 | 18 | 10 |
| Cerebral Vessels | 40 | 0 | 40 | 0 |
| Hypothalamus | 4 | 0 | 4 | 0 |
| Immune System | 25 | 27 | 25 | 27 |
| Nervous System | 27 | 6 | 27 | 6 |

*FIG. 6*

LOCALIZED PHYSIOLOGIC STATUS FROM LUMINOSITY AROUND FINGERTIP OR TOE

BACKGROUND

U.S. Patent Application Publication No. 2005/0014998, entitled METHOD OF DIAGNOSIS OF HUMAN ORGANISM, discusses a human diagnostic method that involves applying an electromagnetic field to fingers contacting an electrode, obtaining visual images of resulting "gas discharge streamers," dividing the visual images into sectors corresponding to various human organs or systems, and projecting the sectors onto a single image formed along the contour of the silhouette of the human body. (See U.S. Patent Application Publication No. 2005/0014998 ¶0010.) The resulting single image can be compared to a reference image, such as to give a diagnosis or evaluate an effect of a therapy. (See id. at ¶0029.)

U.S. Patent Application Publication No. 2006/0084845, entitled METHOD FOR DETERMINING THE ANXIETY LEVEL OF A HUMAN BEING, discusses determining a gas discharge luminosity around a finger in response to an applied electromagnetic field via a glass plate electrode—(1) directly, and (2) in the presence of an intervening polymer film. A level of anxiety of the human being is determined using information from these two different measurements.

U.S. Pat. No. 7,156,866, entitled HOLISTIC METHOD OF TREATING INJURED OR PATHOLOGIC TISSUE WITH A LASER, discusses body energy paths of Eastern medicine, referred to as meridian pathways and Jin Shin Jyutsu energy pathways. (See U.S. Pat. No. 7,156,866 at col. 1, lines 23-26.) It explains that in acupuncture a localized tissue problem area is treated by needling trigger points consisting of nerve endings known to be interconnected along an energy flow path to the localized problem area. (See id. at col. 1, lines 26-29.) It instead uses laser treatment along an energy path to normalize energy flow in a problematic area. (See id. at col. 1, lines 54-62.)

OVERVIEW

This document describes, among other things, systems, devices, and methods that can include a medical device that can be used as a galvanic skin response (GSR) measurement system, such as to acquire skin conductance measurements through a body part, such as the fingertips or toes (for brevity, this document emphasizes operation with respect to one or more fingertips, but it is to be understood that like apparatuses and methods can be additionally or alternatively used with one or more of the subject's toes). The device can measure electromagnetic (field) ("electrical") resistance of the skin. A subject's fingertip can be placed in contact with a transparent electrode, which can be grounded through a power cord. A series of electrical impulses can be applied to the electrode. This can generate a localized electromagnetic field around the finger. Under the influence of this electromagnetic field, and depending on the resistance of the skin of the fingertip, a very small current can be created within the air molecules. This can result in a two-dimensional (2D) spatial response to the electrical field, e.g., in the form of a surrounding small burst of visible or other light, such as in the visible through the ultraviolet range. The light can be captured by a static or dynamic camera image. The captured 2D light spatial response can be assessed for its level of intensity and other analytical criteria that can vary, such as in accordance with the resistance at the fingertip/electrode junction at the time of measurement. For example, the 2D spatial response can be classified, such as either a low, normal, or high response.

Galvanic skin response measurements correlate to the body's electrophysiology. It is believed that the electromagnetic (field) resistance of the human body is not homogenous and that electromagnetic (field) signaling occurs at the cellular level throughout the body. It is believed that the electromagnetic (field) signaling is produced via the mitochondrial cell membrane polarity as it produces energy for the body in the form of adenosine triphosphate (ATP). The ATP process is believed to produce biophotons, packets of electromagnetic energy that can be transferred through the biological system. In particular, nerve fibers throughout the body are believed to produce a higher level of biophotons than other tissue. The fingers and toes are believed to have the highest concentration of tactile nerve fibers in the human body. The hands are believed to have the highest biophotonic production across the body's surface. The relationship of biophotonic signaling at the fingertips or toes to the organs and structures of the body is believed to exist through the neural network of the body. This document includes results from a clinical study that demonstrate a strong correlation from luminosity measurements at the fingertips back to specified organs, systems, or structures elsewhere in the body.

It is also believed that electrical pathways exist over the body. Such electrical pathways can be referred to as meridians. It is believed that the meridians are linked to corresponding particular organs. Imbalances in various organs are believed to manifest themselves as electrophysiological disturbances in the associated meridians. A su-jok method of relating sections of the fingers to their associated meridians can provide an example of a registration system from the major organ systems and structures throughout the body. A capacitive barrier can be used to localize or exclude anxiety response from the overall physiological measurement. Such anxiety can produce perspiration at the fingertips or toes.

The su-jok method of relating sections of the fingers to their associated meridians is mentioned as an example of a registration system from the fingers to the major organ systems and structures throughout the body. The particular registration system that is used can provide a direct measure of the state of the associated organ/system electrophysiology. If the meridian or other electrophysiological pathway associated with a particular body anatomy, location, component, or system, has an electrophysiological imbalance, e.g., a loss of conductive ability, then the portion of the fingertip image for that particular body anatomy, location, component, or system may be dim to non-existent. On the other hand, for excessive conductivity, the portion of the fingertip image may be very bright and potentially very large. The electrophysiology can vary due to many health issues, such as dehydration or loss of electrolytes. It is believed that the fingertip response will change depending on the conductive ability of the metabolic state of the cellular mitochondria along the nerve fibers. A metabolic state of dehydration or loss of electrolytes, for example, can result in a dim and diffuse image pattern not only for the cardiovascular system, but for all organs/systems. The degree of dehydration as measured as explained herein can help a user understand the degree to which the metabolic processes are disturbed, such as to assess the best direction for treatment. The clinical study results presented later in this document are believed to demonstrate the potential for recognizing various different localized abnormal physiological states or disease patterns, providing a meaningful score that a physician can review.

The present systems, devices, and methods can offer a unique measure of electrophysiology characteristics on a systemic level. By analyzing the meridian impedance data, the present systems, devices, and methods can help analyze and evaluate the electrophysiology of the meridians. The reports can provide the user with unprecedented information that can help in the understanding of disease processes while affording the user a more efficient method to assess a subject from a systemic point of view.

The present systems, devices, or methods can be used to validate, correlate, and translate such measurements into an automated report. The results in the report are believed to correlate with physiological abnormalities associated with the disruption of electrophysiological pathways in the body, such as can resolve response information into a physiological status indicator that is particular to a selected particular one of: a cardiovascular system, a gastrointestinal/endocrine system, a respiratory system, a renal system, or a hepatic system. For example, an association with a specified particular body anatomy, location, component, or system that is remote from the finger or toe can involve a particular one of a: cardiovascular system, a gastrointestinal/endocrine system, a respiratory system, a renal system, or a hepatic system. The report can assist a user in triaging subjects for evaluation and testing.

An example can include subject matter (such as an apparatus, a method, a means for performing acts, or a device-readable medium including instructions that, when performed by the device, cause the device to perform acts) that can include obtaining at least two-dimensional (2D) spatial response information of visible or other light around a finger or toe of a subject. The spatial response information obtained at a light detector can be capable of providing spatial information (e.g., about at least first and second spatial dimensions that are orthogonal to each other) or other spatiotemporal information. The light can be obtained in response to electrical stimulation of the finger or toe, which can be sufficient to produce the light at the light detector around the finger or toe.

The spatial response information can be associated to a specified particular body anatomy, location, component, or system that is remote from the finger or toe at which the image information was obtained. The associating can include using information about an electrophysiological pathway for translating the spatial response information into a particularized response indication that is particular to the specified particular body anatomy, location, component, or system. The associating can include radially sectoring the 2D spatial response information. A plurality of parameters can be computed, including using the radially sectored 2D spatial response information to compute at least one of the parameters. At least one of the parameters can be adjusted or compared using information from a clinical knowledge base representative of a population of patients including using at least some patients other than the subject. The at least one adjusted parameter can be used for translating the spatial response information into a particularized response indication that is particular to the specified particular body anatomy, location, component, or system.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, like numerals may describe similar components in different views Like numerals having different letter suffixes may represent different instances of similar components. The drawings illustrate generally, by way of example, but not by way of limitation, various embodiments discussed in the present document.

FIG. 5 shows an illustrative example of a report that can be presented to a user as produced by the ClearView system from Epic Research and Diagnostics, which implements devices and methods such as described in this document.

FIG. 6 shows an illustrative example of another report that can be presented to a user as produced by the ClearView system.

DETAILED DESCRIPTION

Figure 1:
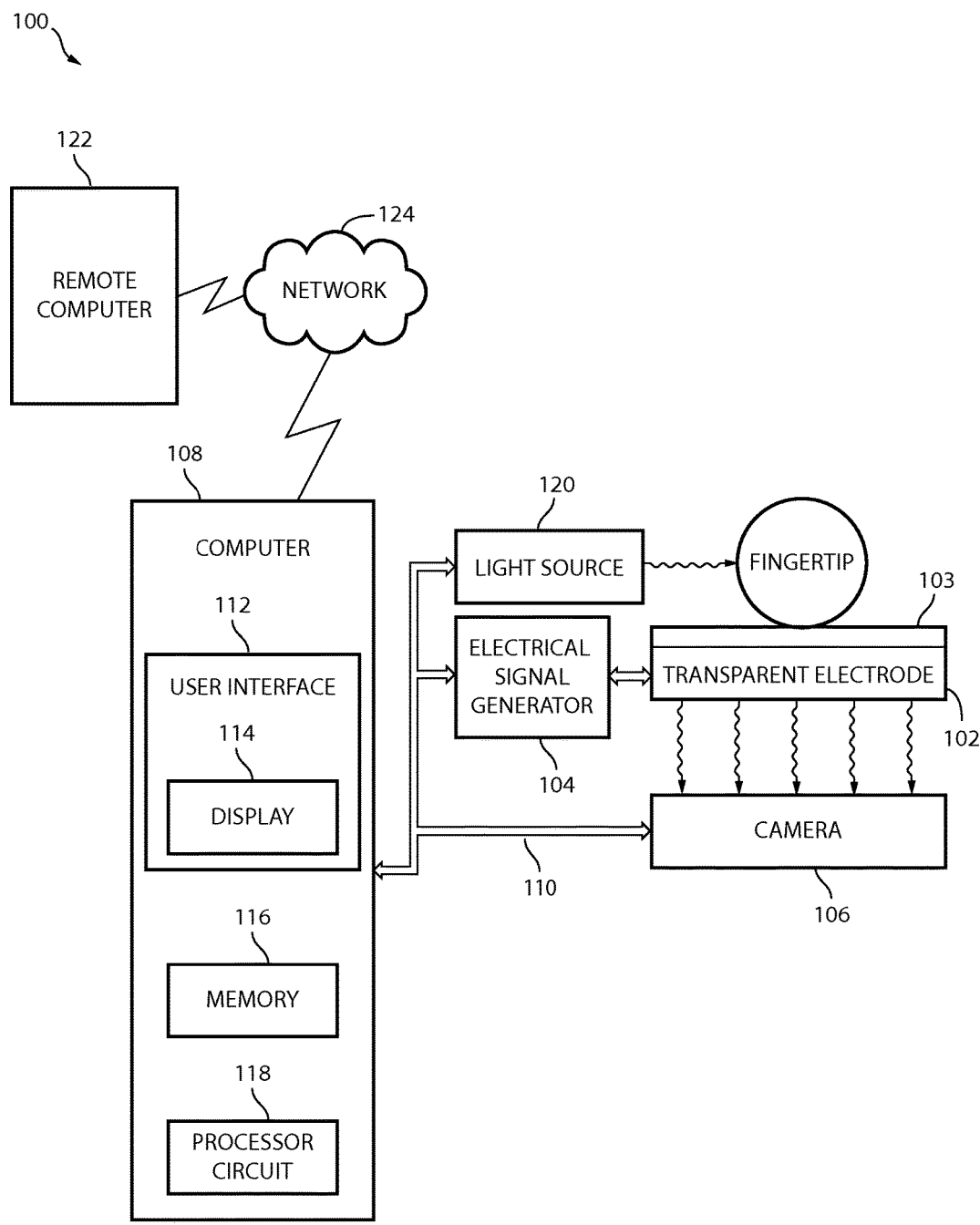
FIG. 1 is a block diagram showing an illustrative example of portions of a system and portions of an environment in which it can be used.

This document describes, among other things, techniques that can include systems or methods of obtaining and processing image or other at least two-dimensional (2D) spatial information about light emitted around a fingertip or toe of a subject, such as in response to electromagnetic (field) ("electrical") stimulation of the subject (for brevity, this document emphasizes operation with respect to one or more fingertips, but it is to be understood that like apparatuses and methods can be additionally or alternatively used with one or more of the subject's toes). Such processing can include mapping the image or other 2D spatial response information to a specified particular body anatomy location, component, or system that is remote from the fingertip at which the image information was obtained (for brevity, this document emphasizes operation with using at least 2D spatial information, but it is to be understood that like apparatuses and methods can additionally or alternatively be used with other at least 2D spatiotemporal information, such as can include a trend over time of at least 2D spatial information, or frequency content of at least 2D spatial information). Such mapping can include using an Eastern medicine meridian mapping or other registration system for associating a luminosity response at the fingertips to a specified particular body anatomy, location, component, or system, such as, for example, associating to a selected particular one of: a cardiovascular system, a gastrointestinal/endocrine system, a respiratory system, a renal system, or a hepatic system. Such processing, registration, or mapping can be used to generate a physiological status indication that is particular to a specified particular body anatomy, location, component, or system. The physiological status indicator can then be provided to a user or an automated process, such as in a textual or pictorial graphic report, or otherwise.

By way of overview, the present techniques can include measuring galvanic skin response (GSR). A subject's fingertip can be placed in contact with a transparent electrode, such as a glass electrode. Electrical or other electromagnetic impulses can be applied to the glass electrode, such as for generating a localized electromagnetic field around the fingertip. Under the influence of this electromagnetic field, and depending on the fingertip skin resistance, ionization can create a very small current within nearby air molecules. This can result in a small burst of visible or other (e.g., ultraviolet) light in a region surrounding the fingertip. An image of this light can be captured, such as by an automated charge-coupled device (CCD) digital camera or other camera or imaging device. The light image (or at least 2D spatial or spatiotemporal response information obtained therefrom) can be image-processed, such as to assess its intensity level or one or more other analytical criteria. The light intensity, for example, can be a function of the resistance at the junction between the fingertip and the electrode at the time of the measurement. The light intensity can be registered, for example, as a low, normal, or high response. As explained in detail below, the light image or other at least 2D spatial or spatiotemporal information can be processed to generate a physiological status indication that is particular to a specified particular body anatomy location, component, or system that is remote from the fingertip. The physiological status indicator can then be provided to a user or an automated process, such as in the form of a textual or pictorial graphical report, or otherwise.

System Overview Example

FIG. 1 is a block diagram showing an example of portions of a system 100 and portions of an environment in which it can be used. In an example, the system 100 can include a transparent electrode 102, which can be configured for receiving a fingertip of a subject, such as on a top surface thereof. An optional removable transparent dielectric barrier 103 can be placed between the fingertip and the electrode 102 during certain measurements, and can be removed or omitted during other measurements.

An electromagnetic (e.g., electrical) signal generator 104 can be electrically coupled to the electrode 102, such as for delivering a suitable electrical (or other electromagnetic) stimulation signal to the fingertip for generating visible or other light (e.g., light in the visible through UV portions of the electromagnetic spectrum) about the fingertip, in response to the electrical stimulation. A camera 106 can provide a light detector to detect an at least 2D spatial response such as an image (or a spatiotemporal response, such as multiple images taken at different times) of the light generated about the fingertip in response to the electrical stimulation of the fingertip. The image information can be communicated to a computer 108, such as via a bus 110.

The computer 108 can include a user or other input/output interface 112, which can allow input from the user or an apparatus or output to the user or an apparatus. The user interface 112 can include a display 114. The computer 108 can include a memory circuit 116, such as for providing a tangible nontransitory medium for storing instructions that can be performed by a signal processor circuit such as processor circuit 118, which can include the memory circuit 116 or can be separate therefrom. The memory circuit 116 can also store image information obtained from the camera, or other 2D spatial or spatiotemporal response information, such as can be derived from such image information. The processor circuit 118 can be configured to provide image processing of the image information obtained from the camera 106. The processor 118 can provide, include, or be coupled to a microcontroller circuit, such as to control or coordinate operation of the electrical signal generator 104, the camera 106, and an optional light-emitting diode (LED) or other light source 120.

The light source 120 can be used to illuminate the subject's fingertip, such as to help align or orient the fingertip as desired on the electrode 102, such as before electrical stimulation and responsive light imaging of the fingertip are performed. The computer 108 can also be configured to communicate with a server or other remote computer 122, such as over a wired or wireless communications or computer network 124, such as a local area network (LAN) or a wide area network (WAN).

Electrical Stimulation and Electrode Example

One approach to GSR would be to measure the relatively slow about 8 to 10 microampere current flow response of the skin, during a time period that is on the order of 10 to 100 seconds, to a small (approximately +2 volt) DC voltage applied to the skin. The current flow can be translated to a 0 to 100 scale with 50 indicating a normal, healthy person response, less than 50 indicating a weak condition, and more than 50 indicating an irritated situation. An "indicator drop" (I.D.) of the conductance number, after slowly rising to its maximum value, can also be determined. For a normal response (about 50), the I.D. occurs within about 1 to 3 seconds and the electrical resistance then maintains a constant value until the full measurement time elapsed (about 10 to 20 sec). When there is an abnormal response (above or below 50), the I.D. can be much longer (about 20 to 60 seconds), depending upon how far away from 50 the maximum conductance reading occurred.

Unlike the above approach, the present techniques need not pass any direct current through the subject's body. Instead, the present techniques can involve measuring light emitted around the finger in response to a small high-frequency alternating current (AC) excitation applied to the subject, such as to the subject's fingertip. The emitted visible or other light can be observed around the entire circumference of the circular or oval contact area of a fingertip, such as for each of the subject's ten fingertips or toes. The intensity of the light emitted around the finger contact area in response to the applied AC electrostimulation can vary according to the skin resistance of the subject.

The AC electrostimulation can be applied to the subject's fingertip by applying the AC electrostimulation potential to the electrode 102, on which the fingertip can rest either directly, or separated therefrom by the dielectric 103. In an example, the electrode 102 can include a transparent glass dielectric portion, upon which the fingertip can be placed, and a transparent conductive portion, such as an indium tin oxide (ITO) coating, to which the AC electrostimulation signal can be applied by the electrical signal generator 104.

When a fingertip is placed on the dielectric glass portion of the electrode 102, two dielectrics (skin and glass) are situated in non-parallel geometry. When an AC electrostimulation voltage is applied to the fingertip skin, breakdown ionization can occur in the air surrounding the fingertip, because of the energy transfer between the charges in the stratum corneum of the fingertip and the dielectric glass portion of the electrode 102. The fingertip can act as a leaky dielectric, and some time may pass before ionizing breakdown of air occurs and light is emitted around the fingertip. The light emitted can vary according to one or more factors, which can include the electrolyte or water content of the fingertip.

In human tissue, the dielectric response is a function of the electric permeability of the skin and the frequency applied to the voltage used when making a measurement. The dielectric properties of the skin decrease with increasing frequency due to the time required for charges to form and migrate across the interfaces and interact with the opposing electrode.

At low frequencies, corresponding to a period on the order of 10 to 100 seconds, conduction current exists, allowing charge to be transferred across the stratum corneum. When the applied voltage is AC at approximately 1000 Hz, the impedance slowly increases with time, but to a smaller degree than when DC voltage is applied over a period of time. Without being bound by theory, this effect can be attributed to the selective permeability nature of the cell membranes (which pass positive ions more easily than negative ions) and the short-circuit channels between the cells. At an approximately 1000 Hz repetition rate, with a positive going square wave voltage pulse of 10 microseconds applied, there is time for the charge to build up then break down. With the about 1 millisecond that exists between the voltage pulses, there is almost sufficient time for the charges to decay before the next pulse arrives. Thus, variations of finger conductance in the high frequency region can be detectable.

The skin, due to its layered structure, can be likened to a capacitor. Each cell in the stratum corneum can have an electrical double layer $10^{-6}$ to $10^{-7}$ cm thick at each cell wall, and these can polarize to give rise to capacitance under the influence of an electric field. For about 100 layers of cell membrane in parallel that make up the stratum corneum, with a dielectric constant of approximately 50, a capacitance on the order of 0.045 $\mu F/cm^2$ can arise, which is within the range observed for skin. This capacitance can vary, such as according to the amount of electrolyte, water, or protein in the skin. The major barrier to the absorption or diffusion of water or electrolytes through the skin is in the outside layers of the epidermis. The overall range of skin permeability is approximately between 0.004 and 600 $\mu cm/min$) and, with age, this permeability decreases. Absorption is most likely along the "spot welds" or desmosomes, which occur at short intervals, creating channels down through the cell membrane layers. These channels act to decrease the leakage resistance between the cell membranes and thus decrease the capacitance of the cell membranes. Diffusion through the desmosomes yields a diffusion coefficient for water of $D=2$ $\mu cm^2/sec$ which is 10 to 20% of the epidermis bulk value.

A cellular membrane includes fixed charge sites, which may be predominantly positively or negatively charged, depending upon the pH of the tissue fluid relative to the iso-electric point (IEP) of the cells. The IEP represents the pH of the solution needed to neutralize the charge state of the surface of the cell. In the instance where the membrane surface is electro-positively charged, H+ ions will be absorbed by the membrane surface. It will be selectively permeable to negative (anions) only. When the membrane becomes electro-negatively charged it is permeable to positive (cations) only. The iso-electric point of a membrane will shift depending on the degree and type of proteins and carbohydrates imbedded in the cell surface. Skin is generally found to be electronegatively charged and is therefore primarily permeable to positive (cations) ions. This selective permeability nature of the skin is similar in effect to the function of a diode in a circuit.

In an example, the electrical signal generator 104 applies a sinusoidal AC electrical signal at a frequency of approximately 1000 Hz, a repetition rate of between about 33 Hz and 1000 Hz, and a duty cycle of between about 5 and 15 microseconds, for a total fingertip electrostimulation exposure duration of between 0.5 second and 32 seconds. The camera 106 can capture light emitted around the fingertip, such as during the entire electrostimulation exposure or a portion thereof, such as in one or a series of images.

Registration, Orientation, and Radial Sector Mapping or Association Example

Figure 2:
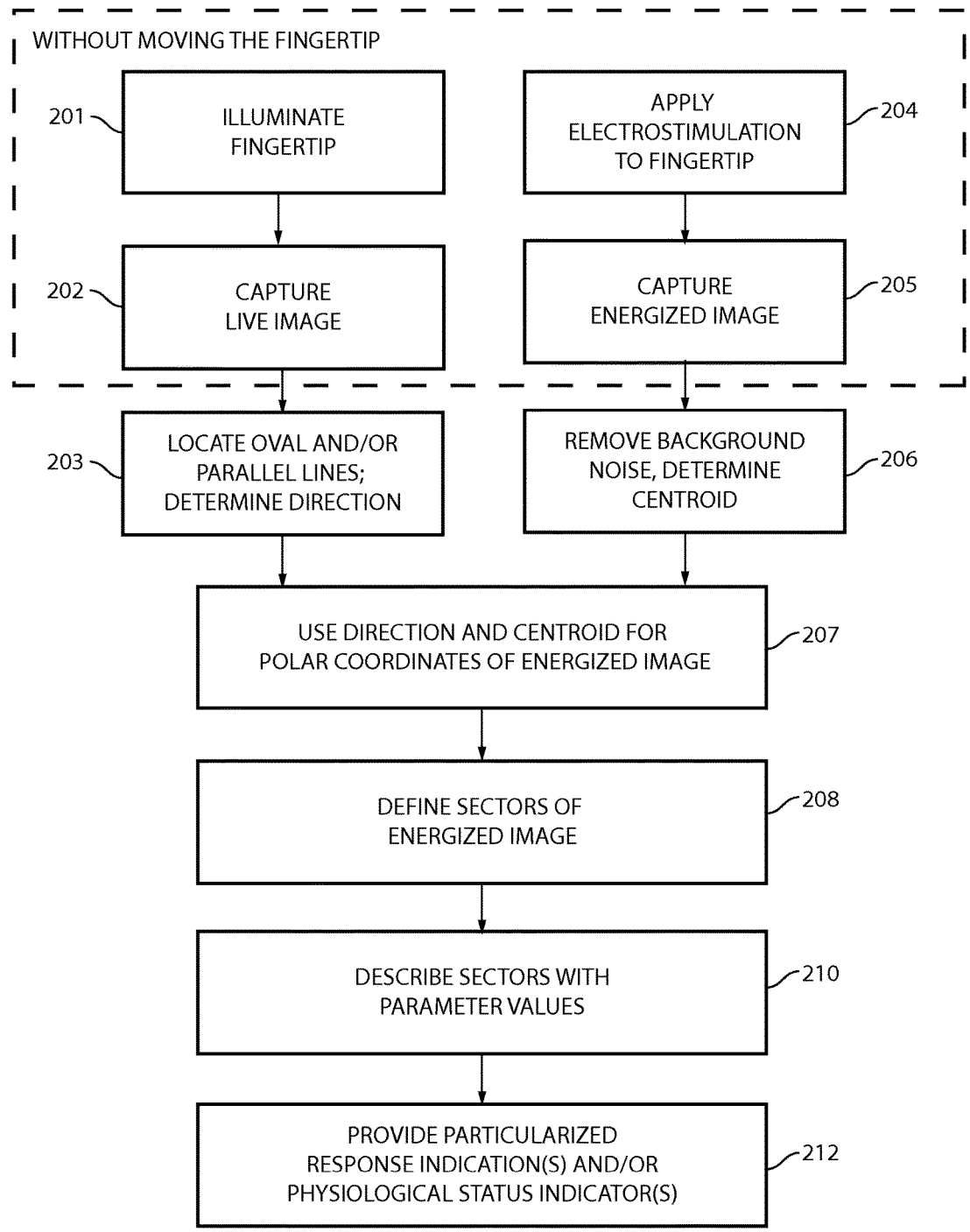
FIG. 2 is a diagram illustrating generally an example of portions of the present technique that can be used to obtain a particularized response indication (such as a physiological status indicator) that is particular to a specified particular body anatomy location, which can be remote from the fingertip.

FIG. 2 is a diagram illustrating generally an example of portions of the present techniques that can be used to obtain a particularized response indication (such as a physiological status indicator) that is particular to the specified particular body anatomy, location, component, or system, which can be remote from the fingertip.

At 201, the fingertip can be illuminated with light from light source 120.

At 202, a "live" image can be captured to help align or orient the fingertip on the electrode 102.

At 203, the user or automated process can use orientation information from the live image to properly orient the energized image, such as rotationally to within a few degrees.

In an example, the processor circuit 118 can be configured to perform image processing that can take the live image of a fingertip and calculate parallel lines along the edges of the live image of the finger as it projects out of the image plane. Such parallel lines can then be aligned to a vertical (longitudinal) center line of an oval. This can allow the live image to be oriented with respect to the oval using such parallel lines and the longitudinal center line of the oval. The parallel lines and/or oval define a reference direction.

When the external edges of the live image of the finger are not clear, or if the finger is very large and therefore there is little of the outward-projecting portion of the finger to be seen in the live image, an automated process may not be able to achieve the correct orientation. In such a case, the user can use information displayed on the display to verify for correct orientation, such as by visually comparing the live image to the energized image and visually assessing the orientation correlation therebetween.

At 204, electrostimulation, such as the AC electrostimulation described above, can be applied by the electrical signal generator 104 to the fingertip, such as to generate visible or other light around the fingertip in response thereto.

At 205, at least two-dimensional (2D) spatial response capture, such as image capture, can be performed. This can include using a light detector such as the camera 106 to acquire the light image obtained in response to the AC electrostimulation. The light image obtained in response to the AC electrostimulation can be referred to as the "energized" image. A corresponding light image obtained without such AC electrostimulation, which can be referred to as the "live" image can also optionally then be obtained, such as under illumination by the light source 120 (without accompanying AC electrostimulation). The live image can later be used to orient the later-obtained energized image, if desired.

At 206, a baseline determination can be made, such as to determine a level of background noise that is present in the light image. First, a centroid of the image can be determined and deemed to correspond to the center of the fingertip. Then, the background noise can be determined, such as by using the processor circuit 118 to perform image-processing of the image pixels from the camera 106 to locate the highest gradient in light intensity in the image. This highest gradient in light intensity will occur at the inner edge of the image where the outer perimeter of the fingertip meets the electrode 102 (or the dielectric 103) upon which the fingertip is placed. Within such perimeter, any light detected in the image can be deemed noise, since insufficient air is present there to generate an ionizing light response to the AC electrostimulation. All lower intensity pixels within such perimeter can be removed from the image, such as by iteratively processing the image from the centroid of the fingertip outward. Such lower intensity pixel removal can continue iteratively until a consistent radius from the centroid of the fingertip to the highest gradient in light intensity is obtained. The magnitude of this radius vector can then be calculated, such as can be expressed as the number of pixels from the centroid of the fingertip image to the inner edge of the image.

At 207, the energized image can be rotationally or translationally oriented, such as automatically, without requiring user intervention. This can be accomplished via signal processing by placing an oval over the live image at a center, which can be calculated as the centroid obtained from the pixels of the live image. The live image centroid can be deemed to correspond exactly to the centroid of the energized image, and these two centroids can be overlaid. The "live" image can be used to automatically (e.g., without requiring user intervention) orient (e.g., at least one of rotationally or translationally) an oval onto the "energized" image. The oval can be used to establish the reference direction for polar coordinates on the energized image so that a radial sectoring system can be placed on the energized image in the correct orientation.

In an example, the live image can allow the user (or an automated process) to visualize the finger, including how it projects out of the image plane. This can permit the user (or an automated process) to visualize the orientation of the finger in the live image.

At 208, the at least two-dimensional (2D) spatial response, such as the energized image, can be registered to the body, such as for mapping the light intensity information of particular radial sectors of the image (e.g., referenced to the centroid of the image) to a respective corresponding particular body anatomy, location, component, or system, which can be remote from the fingertip.

According to an example of the radial sectoring system, the fingers can be numbered, starting with the thumb, which can be designated finger number one, the forefinger (index finger) can be designated finger number two, and so forth. Table 1 illustrates: (1) individual fingers; (2) examples of radial sectors of the various individual fingers; (3) examples of angles defining such radial sectors; and (4) particular body anatomy location, component, or system corresponding to the respective radial sectors. In Table 1, the angles describe angular locations of radial rays extending radially outward from the centroid of the fingertip image, with 0° corresponding to the reference direction, and with the angle value increasing in a clockwise direction therefrom.

TABLE 1

Example of Radial Sectoring System and Association or Mapping to Body Anatomy

| Finger & Sector Number | Finger | Angles (degrees) | Body Anatomy |
|---|---|---|---|
| 1L1 | ThumbLeft | 280 to 315 | Right Eye |
| 1L2 | ThumbLeft | 260 to 280 | Right Ear, Nose Maxillary Sinus |
| 1L3 | ThumbLeft | 225 to 260 | Jaw, Teeth Right Side |
| 1L4 | ThumbLeft | 135 to 225 | Throat, Larynx, Trachea, Thyroid |
| 1L5 | ThumbLeft | 100 to 135 | Jaw, Teeth Left Side |
| 1L6 | ThumbLeft | 80 to 100 | Left Ear, Nose, Maxillary Sinus |
| 1L7 | ThumbLeft | 45 to 80 | Left Eye |
| 1L8 | ThumbLeft | 315 to 45 | Cerebral Zone (Cortex) |
| 1R1 | ThumbRight | 280 to 315 | Right Eye |
| 1R2 | ThumbRight | 260 to 280 | Right Ear, Nose Maxillary Sinus |
| 1R3 | ThumbRight | 225 to 260 | Jaw, Teeth Right Side |
| 1R4 | ThumbRight | 135 to 225 | Throat, Larynx, Trachea, Thyroid |
| 1R5 | ThumbRight | 100 to 135 | Jaw, Teeth Left Side |
| 1R6 | ThumbRight | 80 to 100 | Left Ear, Nose, Maxillary Sinus |
| 1R7 | ThumbRight | 45 to 80 | Left Eye |
| 1R8 | ThumbRight | 315 to 45 | Cerebral Zone (Cortex) |
| 2L1 | ForefingerLeft | 260 to 280 | Descending Colon |
| 2L2 | ForefingerLeft | 220 to 260 | Sigmoid Colon |
| 2L3 | ForefingerLeft | 190 to 220 | Rectum |
| 2L4 | ForefingerLeft | 170 to 190 | Coccyx, Pelvis Minor |
| 2L5 | ForefingerLeft | 140 to 170 | Sacrum |
| 2L6 | ForefingerLeft | 100 to 140 | Lumbar Zone |
| 2L7 | ForefingerLeft | 85 to 100 | Thorax |
| 2L8 | ForefingerLeft | 45 to 80 | Cervical |
| 2L9 | ForefingerLeft | 280 to 45 | Transverse Colon |
| 2R1 | ForefingerRight | 280 to 315 | Cervical |
| 2R2 | ForefingerRight | 260 to 280 | Thorax |
| 2R3 | ForefingerRight | 220 to 260 | Lumbar |
| 2R4 | ForefingerRight | 190 to 220 | Sacrum |
| 2R5 | ForefingerRight | 170 to 190 | Coccyx Pelvis |
| 2R6 | ForefingerRight | 130 to 170 | Bling Gut |
| 2R7 | ForefingerRight | 100 to 130 | Appendix |
| 2R8 | ForefingerRight | 80 to 100 | Ascending Colon |
| 2R9 | ForefingerRight | 315 to 80 | Transverse Colon |
| 3R1 | MiddleLeft | 210 to 330 | Cardiovascular System |
| 3R2 | MiddleLeft | 180 to 210 | Kidney |
| 3R3 | MiddleLeft | 150 to 180 | Liver |
| 3R4 | MiddleLeft | 100 to 150 | Abdominal Area |
| 3R5 | MiddleLeft | 80 to 100 | Immune system |
| 3R6 | MiddleLeft | 30 to 80 | Thorax & Respiratory |
| 3R7 | MiddleLeft | 330 to 30 | Cerebral Vessels |
| 3R1 | MiddleRight | 280 to 330 | Thorax & Respiratory |
| 3R2 | MiddleRight | 260 to 280 | Immune System |
| 3R3 | MiddleRight | 210 to 260 | Gall Bladder |
| 3R4 | MiddleRight | 180 to 210 | Liver |
| 3R5 | MiddleRight | 150 to 180 | Kidney |
| 3R6 | MiddleRight | 30 to 150 | Cardiovascular System |
| 3R7 | MiddleRight | 330 to 30 | Cerebral Vessels |
| 4L1 | RingLeft | 280 to 315 | Hypothalamus |
| 4L2 | RingLeft | 260 to 280 | Nervous System |
| 4L3 | RingLeft | 225 to 260 | Spleen |
| 4L4 | RingLeft | 150 to 225 | Uro-Genital |
| 4L5 | RingLeft | 130 to 150 | Adrenal |
| 4L6 | RingLeft | 110 to 130 | Pancreas |
| 4L7 | RingLeft | 80 to 110 | Thyroid |
| 4L8 | RingLeft | 45 to 80 | Hypophysis-Pituitary |
| 4L9 | RingLeft | 315 to 45 | Epiphysis-Pineal |
| 4R1 | RingRight | 280 to 315 | Pituitary |
| 4R2 | RingRight | 250 to 280 | Thyroid |
| 4R3 | RingRight | 230 to 250 | Pancreas |

TABLE 1-continued

Example of Radial Sectoring System and Association or Mapping to Body Anatomy

| Finger & Sector Number | Finger | Angles (degrees) | Body Anatomy |
|---|---|---|---|
| 4R4 | RingRight | 210 to 230 | Adrenal |
| 4R5 | RingRight | 135 to 210 | Uro-Genital |
| 4R6 | RingRight | 100 to 135 | Spleen |
| 4R7 | RingRight | 80 to 100 | Nervous System |
| 4R8 | RingRight | 45 to 80 | Hypothalamus |
| 4R9 | RingRight | 315 to 45 | Pineal |
| 5L1 | LittleLeft | 270 to 315 | Left Heart |
| 5L2 | LittleLeft | 225 to 270 | Left Uro-Kidney |
| 5L3 | LittleLeft | 135 to 225 | Left Breast/Respiratory System |
| 5L4 | LittleLeft | 90 to 135 | Jejunum |
| 5L5 | LittleLeft | 45 to 90 | Right heart |
| 5L6 | LittleLeft | 315 to 45 | Coronary Vessels |
| 5R1 | LittleRight | 270 to 315 | Duodenum |
| 5R2 | LittleRight | 225 to 270 | Ileum |
| 5R3 | LittleRight | 135 to 225 | Right Breast, Respiratory System |
| 5R4 | LittleRight | 90 to 135 | Right Uro-Kidney |
| 5R5 | LittleRight | 45 to 90 | Heart |
| 5R6 | LittleRight | 315 to 45 | Coronary Vessels |

At 210, the properly oriented energized image of a fingertip can be analyzed, such as by using automated image processing that can be provided by the processor circuit 118, such as described further below.

At 212, a result of analysis at 210 is provided as a particularized response indication (such as a physiological status indicator) that is particular to the specified particular body anatomy, location, component, or system, which can be remote from the fingertip.

Image Analysis Example: Parameter Determination

Figure 3:
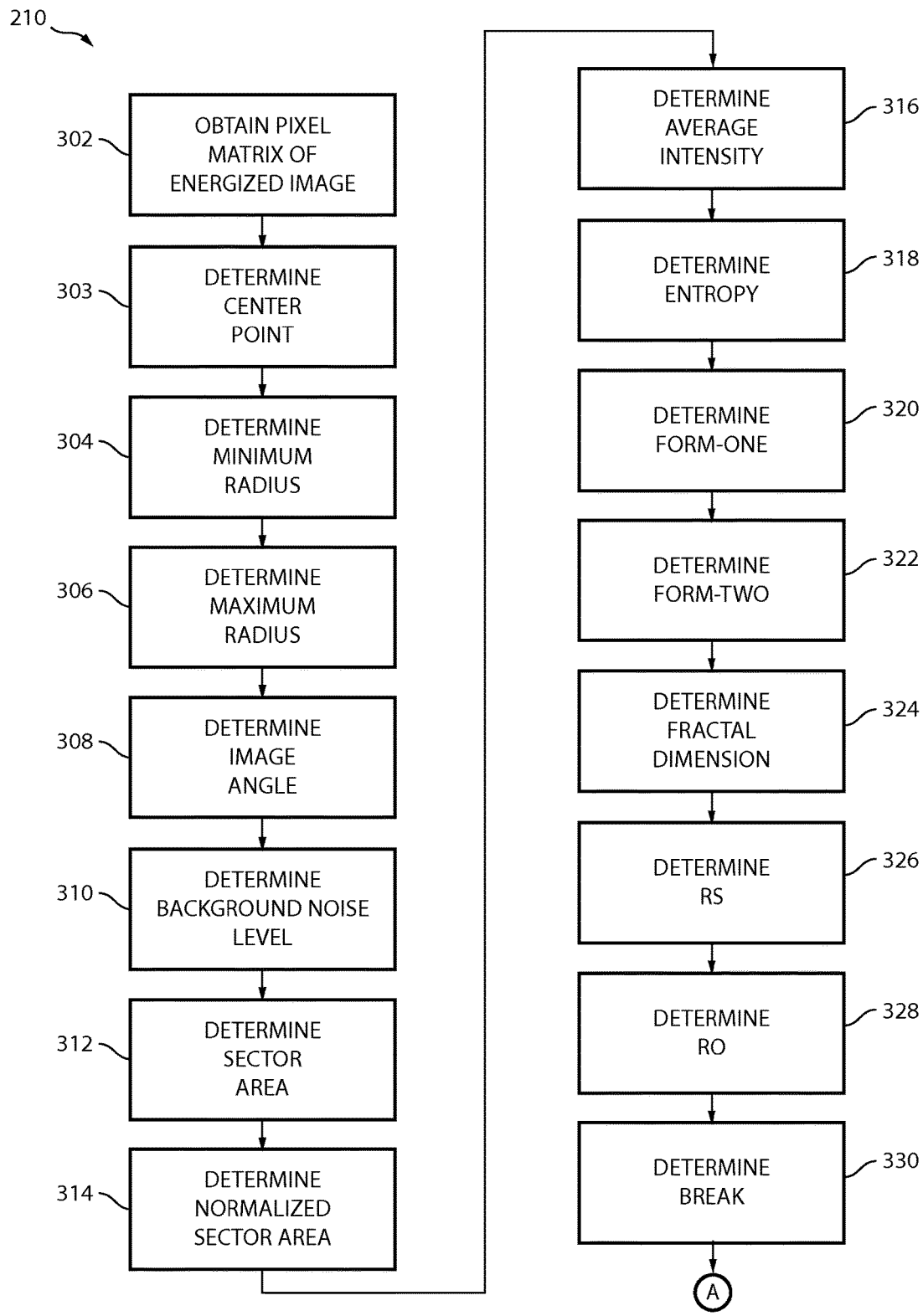
FIG. 3 shows an illustrative example of portions of an image-analysis technique.

FIG. 3 shows an example of such an image-analysis technique. At 302, for image analysis, the energized image can be broken down into a pixel matrix, for an illustrative (non-limiting) example, such as an x=320 by y=240 pixel matrix representing the respective x and y positions of pixels in the image. Each pixel can include data representing light intensity observed at that pixel location. From the pixel information, in an example, various analysis parameters can be determined, such as by automated image processing of the energized image using the processor circuit 118. In an example, such analysis parameters can include Normalized Sector Area, Average Intensity, Form-One, Form-Two, Entropy, Fractal, Reference-Subjective, Reference-Objective, and Break, such as described further below.

At 303, a Center Point location parameter of the energized image can be obtained or determined. In an example, the Center Point can be determined by first determining contour points of the fingertip boundaries. The contour points can be determined by (e.g., working out from the true center of the image) selecting pixels having an intensity exceeding a specified intensity threshold value. An ellipse can then be fitted to such contour points, such as by using a least-squares analysis to perform the fitting. The ellipse fitting can be iteratively repeated, if desired. At each iteration, one or more outliers among the contour points can be removed. The midpoint of the ellipse can be determined and deemed to be the Center Point of the energized image.

At 304, a Minimum Radius parameter of the fingertip energized image can be determined, such as by automated image processing using the processor circuit 118. The Minimum Radius parameter of the image can be determined as the smaller principal axis of the ellipse fitted as described above.

At 306, a Maximum Radius of the fingertip energized image can be determined, such as by automated image processing using the processor circuit 118. The Maximum Radius of the image can be determined as the larger principal axis of the ellipse fitted as described above.

At 308, an Image Angle parameter can be determined, such as by automated image processing using the processor circuit 118. The Image Angle can be given by the angle between the major axis and the reference direction on the energized image. If the ellipse is close to a circle (which is the case when the ratio of the major axis to the minor axis is at or near 1.0), then the Image Angle can be declared to be zero.

At 310, a Background Noise Level parameter can be determined, such as by determining a threshold intensity level at which only a specified amount (e.g., 0.002% of the pixels in the center region of the image) exceed the threshold intensity level. In an example, this Background Noise Level can be determined in the center region of the image, which can be taken as the interior of the ellipse (e.g., within the Minimum Radius), with the ellipse fitted such as described above with respect to 303). This threshold intensity level can be declared to be the Background Noise Level. The center region of the image can be used because this should be an area completely devoid of light and therefore representative of what the background of the image should look like.

In an example, to calculate the Background Noise Level, intensities can be determined for all "lit" pixels within the center region area that is defined by the ellipse fitted as described above with respect to 303. An iterative calculation can be used to iteratively remove portions of the lit pixels within the center region. In an example, percentages of the lit pixels can removed, such as based on their intensities, until only a specified target amount (e.g. 0.002%) of the originally-present lit pixels in that center region remain. So, in an illustrative example, if there are 100 lit pixels to start with, of varying intensities, in a first pass through, all lit pixels with intensities less than a threshold value (e.g., threshold value=20) can be cleared. Those lit pixels that remain, if greater than the specified target amount of 0.002% of the original number of lit pixels that were present in the center region, can be processed in another pass, in which all lit pixels having an intensity value of less than a higher threshold value (e.g., threshold value=30) can be removed. If greater than the specified target amount of 0.002% of the original number of lit pixels in the center region are still present in the center region, then another pass can be made. This iterative process can continue until the specified target amount of only 0.002% of the original number of lit pixels within the center region remain. The corresponding intensity level can be declared to be the Background Noise Level. In an example, the Background Noise level can be between 30 and 45, in most cases.

An Inner Radius can be determined, as explained above, such as after the Background Noise has been subtracted from the image. The remaining image has an Inner Radius that is described by the distance from the center point to the first pixel, in the radial direction from the center, that exceeds the background noise level. This Inner Radius dimension will be variable along the inner edge of the image due to the size and shape of the finger that created the image. For each calculation, the inner radial distance can be calculated.

At 312 of FIG. 3, a Sector Area parameter of a particular radial sector (or a specified subset of the radial sectors that is smaller than the set of all radial sectors) can be computed, such as for one or more radial sectors of the energized image. A radial sector can be given by an area between rays, such as adjacent rays, emanating radially outward from the Center Point of the 2D energized image. The Sector Area of a particular sector can be determined as the number of pixels within a particular sector and within the fitted ellipse, having an intensity exceeding a specified value, such as exceeding a specified value of the Background Noise Level.

At 314, a Normalized Sector Area parameter of a particular sector (or a specified subset of the radial sectors that is smaller than the set of all radial sectors) can be computed, such as for one or more radial sectors of the energized image. In an example, the Normalized Sector Area can be given by the following relationship:

$$AN = A * \frac{360/S}{\theta}$$

where AN is the normalized sector area
A is the sector area
S is the quantity of sectors
$\theta$ is the radial angle of the sector between end rays At 316, an Average Intensity parameter of a particular sector (or a specified subset of the radial sectors that is smaller than the set of all radial sectors) can be computed, such as for one or more radial sectors of the energized image. In an example, the Average Intensity of a particular sector can be determined by dividing the sum of intensities of all pixels in a particular sector by the number of pixels given by the Sector Area for that sector.

At 318, an Entropy parameter of a particular sector (or a specified subset of the radial sectors that is smaller than the set of all radial sectors) can be computed, such as for one or more radial sectors of the energized image. This can include computing a Shannon Entropy along a profile. The profile can be created by traversing the image radially with a sweep ray extending from the Center Point of the fitted ellipse, and sweeping the ray clockwise with respect to the Center Point of the fitted ellipse, which can serve as a fixed reference. The clockwise sweep of the sweep ray can be performed in steps, such as of ¼ of an angular degree, in an illustrative example, and the profile (and corresponding Shannon Entropy) can be determined along the sweep ray at each such step.

Figure 4:
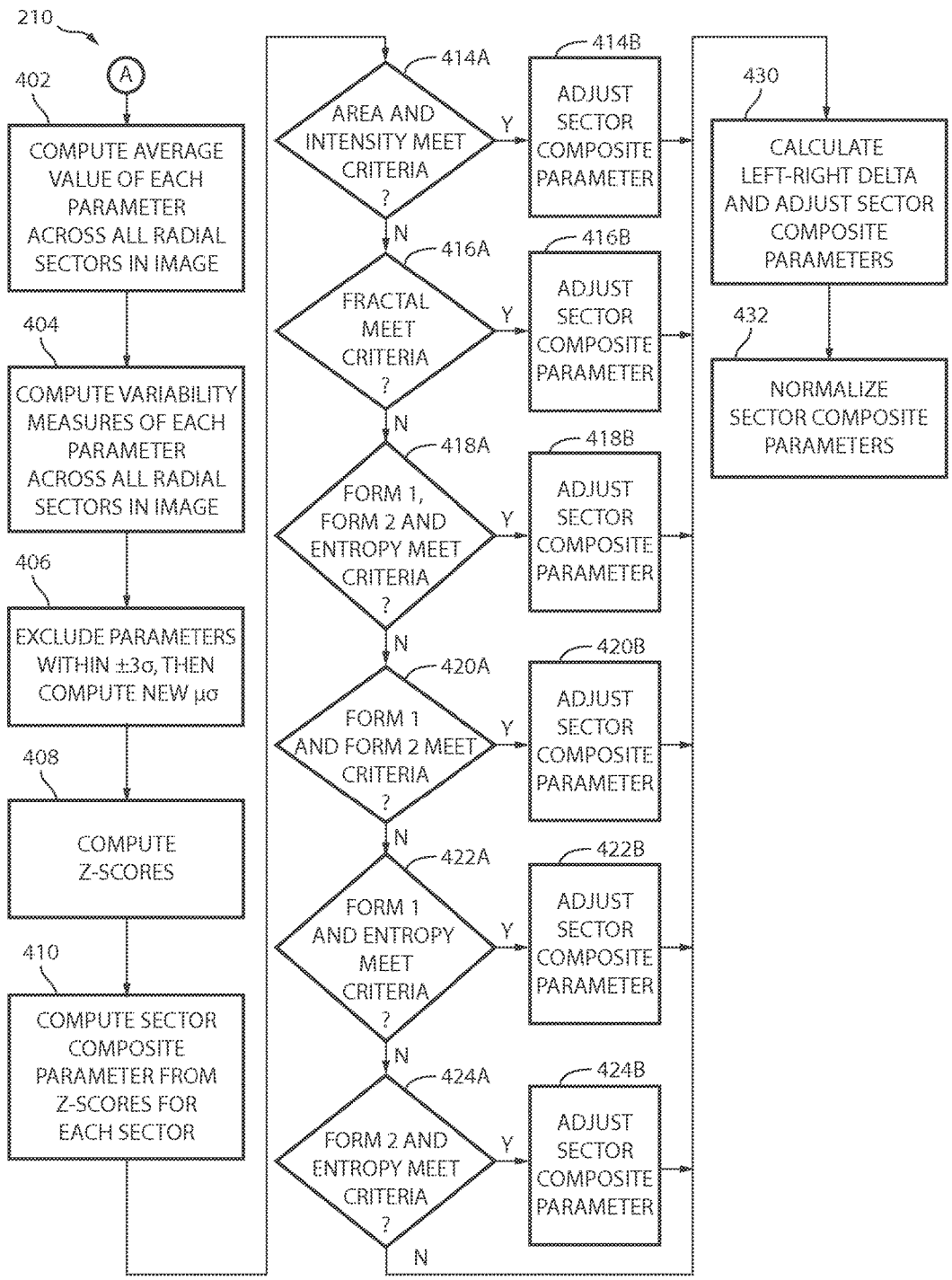
FIG. 4 shows an illustrative example of portions of an image-analysis technique.

For each of the resulting (e.g., 360*4=1440) angles, an image profile can be computed, such as by selecting the pixels exceeding the Background Noise Level (e.g., as explained above with respect to FIG. 4) that intersect with the sweep ray at one of the 1440 (or other number of) angles and centered at the ellipse midpoint. Thus, a particular image profile can include an angle, a set of pixels extending radially along the profile at that angle, and the intensities associated with the profile pixels.

An Entropy for a particular sector (or a specified subset of the radial sectors that is smaller than the set of all radial sectors) can be computed, such as by first computing an Entropy for each individual profile within that particular sector, and then averaging or otherwise determining a central tendency of each individual profiles to obtain a composite profile for that particular sector. For various pixel positions i along the radial profile (where the integer i=1, 2, . . . n, and n is the total number of pixels in the radial profile), the Entropy can be expressed as a radial vector E given by the following relationship:

$$E = -\sum_{i=1}^{n} \mu_i * (\log_{10} \mu_i)$$

where E is the entropy $$\mu_i = \frac{\Delta I_i}{\sum_{i=1}^{n} \Delta I_i}$$

$\Delta I_i$ is pixel intensity above the background noise level

At 320, a Form-One parameter of a particular sector (or a specified subset of the radial sectors that is smaller than the set of all radial sectors) can be computed, such as for one or more radial sectors of the energized image. The particular image profiles determined at the various (e.g., 1440 angles) angular positions, as explained above, can be used in determining the Form-One parameter. The active area of the fingertip image can be divided into adjacent concentric regions (e.g., annular regions or, in the center, a disk) that are separated from each other by concentric circular rings (of different radii), which can be commonly coaxially centered at the Center Point of the ellipse. In an example, three such concentric rings can be used to compute three Form-One parameters, with corresponding progressively increasing radii of R1, R2, and R3 to define boundaries of three concentric regions having respective areas A1 (area of a disk bounded by R1), A2 (area of a ring between R1 and R2), and A3 (area of a ring between R2 and R3). In an example, the Form-One parameter of a particular sector can be expressed using multiple Form-One parameters, such as Form-One$_1$ for area A1, Form-One$_2$ for area A2, and Form-One$_3$ for area A3.

In an example, Form-One$_1$, Form-One$_2$, and Form-One$_3$ for each area A1, A2, and A3 can represent derivative parameters, respectively providing an indication of the amount of change in pixel intensity along each radial image profile within the respective concentric region A1, A2, and A3. Form-One for each area (e.g., A1, A2, and A3) can be determined by computing the maximum value of the derivative along the image profile within the respective concentric region, A1, A2, and A3 as indicated above. In an example, the Form-One parameters for a particular sector can be expressed as follows:

$$F1_r = \frac{4\pi L_r}{S_r}$$

where $F1_r$ is the Form-One parameter for a region r
$L_r$ is the perimeter length (in pixel count) for region r $$S_r = \Delta I_i \Big/ \sum_{i=min}^{i=max} \Delta I_i$$

min and max correspond to the region r
$\Delta I_i$ is the pixel intensity above the background noise level At 322, Form-Two can be calculated using a similar calculation; however it can be carried out for the concentric region having a radius greater than R3.

At 324, a Fractal dimension parameter of a particular sector (or a specified subset of the radial sectors that is smaller than the set of all radial sectors) can be computed, such as for one or more radial sectors of the energized image. The Fractal parameter can be determined by computing a mathematical fractal dimension, such as using a box-counting method for a two-dimensional area. The Fractal parameter can be represented by:

$$M = \frac{2\pi L}{R_{avg}}$$

where M is the Fractal dimension parameter

L is the perimeter length (in pixel count) of the sector $$R_{avg} = \left(\frac{1}{n}\right)\sum_{i=1}^{n} R_i$$

$R_i$ is the inner radius (see step 304 of FIG. 3)

i is a radial profile of the n radial profiles of the sector

At 326, a Reference-Subjective parameter (RS) for a particular sector (or a specified subset of the radial sectors that is smaller than the set of all radial sectors) can be computed, such as for one or more radial sectors of the energized image. RS can provide a comparison measure between a subject's image sector and a corresponding sector of a subject-specific calibration image (e.g., a calibration image that has been taken on the same day as the subject images). The RS comparison can be determined both with and without the dielectric 103 in place. In an example, the RS parameter can be determined for a particular sector using the following relationship:

$$RS_s = \frac{\left\{\frac{\overline{SI_s}}{\overline{CI_s}} - 0.5\right\}}{\frac{\log(SA_s)}{SP_s + \varepsilon} \Big/ \frac{\log(CA_s)}{CP_s + \varepsilon}}$$

where RS is the reference-subjective parameter s identifies one sector of interest $\overline{SI_s}$ is an average intensity of sector s of the subject image $\overline{CI_s}$ is an average intensity of sector s of a calibration image the value 0.05 can be subtracted for normalization $SA_s$ is the quantity of active pixels in sector s of the subject image $SP_s$ is the total quantity of pixels in sector s of the subject image $CA_s$ is the quantity of active pixels in sector s of the calibration image $CP_s$ is the total quantity of pixels in sector s of the calibration image the value $\varepsilon$ can be set to a value (e.g., $10^{-4}$ to ensure stability)

At 328, a Reference-Objective parameter (RO) for a particular sector (or a specified subset of the radial sectors that is smaller than the set of all radial sectors) can be computed, such as for one or more radial sectors of the energized image. The RO parameter can also provide a comparison measure between a subject's image sector and a corresponding sector of a "perfect" subject image (such as has been previously stored and retrieved from a database). The RO comparison can be determined both with and without the dielectric 103 in place, just as described above for RS, except that the determination of RO can differ by substituting a population-composite healthy person image for the subject-specific calibration image used in the RS computation. The population-composite healthy person image can be determined by generating a composite image from a sample (e.g., of tens of thousands) of human fingertip images from known or presumed healthy subjects.

At 330, a Break parameter can be determined. The Break parameter, can represent a gap, providing an indication of whether there is a gap in the inner ring bounding a particular concentric region. A gap can be declared to exist when one or more pixels along such inner ring has an intensity that falls below a threshold value, such as the Background Noise Level. The value of the Break parameter can correspond to the size (e.g., the circumferential length along the inner ring) of such gap, if any. If a gap exists, the Break parameter can be assigned a specified value, such as a value between 0 and 10.

Image Analysis Example: Analysis Process & Rules

By way of overview, in an example, each of the parameters described above with respect to FIG. 3 (e.g., Center Point, Inner Radius, Fractal, Entropy, etc., which can be denoted ($x_1$, $x_2$, . . . , $x_n$)) can be calculated from the energized image, assessed for normality within the dataset (e.g., using information from a clinical knowledge base representative of a population of patients including using at least some patients other than the subject), and statistical outliers can be discarded (or otherwise adjusted).

After such processing, if any, the parameters described above can be combined, for a particular radial sector, into a sector composite parameter for that radial sector, such as by a weighted linear combination (e.g., $y = a \cdot z_1 + b \cdot z_2 + c \cdot z_3 + \ldots + y \cdot z_n$, where a, b, c, etc. are scaling coefficients, and $z_1 \ldots z_n$ are the normal distribution z-scores associated with the parameters described above with respect to FIG. 3.) The normal distribution z-scores can be determined using information from a clinical knowledge base representative of a population of patients including using at least some patients other than the subject.

The sector composite parameter then can be scaled, such as to fit within a defined scale (e.g., a scale from 0 to 5, or a scale from 0 to 25, which can be defined by a population to which the subject is being compared (e.g., using information from a clinical knowledge base representative of a population of patients including using at least some patients other than the subject), or by other sector composite parameters associated with the same subject). An example is explained in more detail below with respect to FIG. 4. The acts described with respect to FIG. 4 can be applied after each of the parameters described above with respect to FIG. 3 has been calculated for each of the radial sectors.

At 402, for each parameter ($x_1$, $x_2$, . . . , $x_n$) described above with respect to FIG. 3, a corresponding average value ($\mu_1$, $\mu_2$, . . . , $\mu_n$) or other central tendency of that parameter can be computed across all radial sectors in the energized image.

At 404, for each parameter ($x_1$, $x_2$, . . . , $x_n$) described above with respect to FIG. 3, a corresponding standard deviation value ($\sigma_1$, $\sigma_2$, . . . , $\sigma_n$) (or variance, or other measure of dispersion or variability) of that parameter can be computed across all radial sectors in the energized image. Then, a first variability range (e.g., of +/−one standard deviation) of that parameter across all the radial sectors in the energized image can be calculated. Then, a second variability range (e.g., of +/−three standard deviations) of that parameter across all the radial sectors in the energized image can be calculated.

At 406, for each radial sector, any parameters that fall within the second variability range (e.g., fall within +/−three standard deviations) can be excluded from the next average and standard deviation calculation. From those parameters that have not been so excluded, and a second average and a second standard deviation can be computed across non-excluded radial sectors.

At 408, a normal distribution z-value (also called a z-score, where $z_1=(x_1-\mu_1)/\sigma_1$) can be calculated for all parameters $(x_1, x_2, \ldots, x_n)$, for all sectors, including those that were excluded from the previous average and standard deviation calculation, of the energized image—but using the applied second average and the applied second standard deviation determined at 406, instead of the average and standard deviation determined at 402 and 404.

At 410, for each radial sector, the z-scores described above at 408 can be combined into a sector composite parameter, such as by a weighted linear combination, for example:

$$y = a \cdot z_1 + b \cdot z_2 + c \cdot z_3 + \ldots + x \cdot z_n$$

where y is the sector composite parameter
  a, b, c, etc. are scaling weights
  $z_1 \ldots z_n$ are unscaled z-scores described above at 408

In an example, the scaling weights associated with the corresponding unscaled z-scores of the parameters can be as follows:
  Area weight=0.5
  Intensity weight=25
  Entropy weight=1500
  Form-One weight=300
  Form-Two weight=300
  RS weight=3000
  Fractal weight=225
  Break weight=5000

The Break weight can be applied as an on/off rule: it can be applied if a break is present, and not applied if the break is not present. The Break weight can be scaled by a specified value, such as a value that can be between 0 and 10.

At 414-424, one or more rules can then be applied to the sector composite parameter, based upon the z-scores of the parameters associated with that radial sector.

At 414A, if any radial sector meets one or more specified criteria, such as a z-score greater than or equal to a specified value (e.g., 0.9) for both Area and Intensity, then at 414B the sector composite parameter for that radial sector can be adjusted, such as by adding an additional amount (e.g., 5000) to the sector composite parameter for that radial sector of the energized image.

At 416A, if any radial sector meets one or more specified criteria, such as a z-score greater than or equal to 0.9 for Fractal, then at 416B the sector composite parameter for that radial sector can be adjusted, such as by adding an additional amount (e.g., 10,000) to the sector composite parameter for that radial sector of the energized image.

At 418A, if any radial sector meets one or more specified criteria, such as a z-score greater than or equal to 0.9 for each of Form-One, Form-Two, and Entropy, then at 418B the sector composite parameter for that radial sector can be adjusted, such as by adding an additional amount (e.g., 7000) to the sector composite parameter for that radial sector of the energized image.

At 420A, if any radial sector meets one or more specified criteria, such as a z-score greater than or equal to 0.9 for each of Form-One and Form-Two, then at 420B the sector composite parameter for that radial sector can be adjusted, such as by adding an additional amount (e.g., 5000) to the sector composite parameter for that radial sector of the energized image.

At 422A, if any radial sector meets one or more specified criteria, such as a z-score greater than or equal to 0.9 for each of Form-One and Entropy, then at 422B the sector composite parameter for that radial sector can be adjusted, such as by adding an additional amount (e.g., 7000) to the sector composite parameter for that radial sector of the energized image.

At 424A, if any radial sector meets one or more specified criteria, such as a z-score greater than or equal to 0.9 for each of Form-Two and Entropy, then at 424B the sector composite parameter for that radial sector can be adjusted, such as by adding an additional amount (e.g., 10,000) to the sector composite parameter for that radial sector of the energized image.

At 414-424, the one or more rules can be evaluated (in the priority listed and shown in FIG. 4) such that only one of these rules is actually applied and given effect, such that there is no duplicative adjustment to the sector composite parameter from more than one of the rules of 414-424.

At 430, for those body anatomy organs or systems in Table 1 that correspond to both a radial sector of the left hand and a radial sector of the right hand, a left to right differential sector composite parameter ("delta") between the respective sector composite parameters for such left-hand and right-hand radial sectors can be computed. If the delta exceeds 50% of the value of either of the respective sector composite parameters for such left-hand and right-hand radial sectors corresponding to the same body anatomy organ or system, then an additional amount (e.g., 20,000) can be added to the respective sector composite parameters for such left-hand and right-hand radial sectors corresponding to the same body anatomy organ or system.

At 432, the sector composite parameter for each radial sector of the energized image, after adjusting as described above with respect to 414-430, can be scaled, such as by multiplying or dividing the value of the sector composite parameter by a specified normalizing amount (e.g., dividing by 100).

At 434, the resulting normalized sector composite parameter can be compared to a within-subject curve (e.g., a normal distribution curve compiled from all of the sector composite parameters of the same subject) and also fit to a population-based curve (e.g., a normal distribution curve for the same sector composite parameter from a comparable population or subpopulation of subjects, such as using information from a clinical knowledge base representative of a population of patients including using at least some patients other than the subject). The population-based curve can be based on a comparable subpopulation of patients, such as based upon one or more factors such as medical history, gender, race, or age). The location of the sector composite parameter within the within-subject curve can be scaled and reported to the user. The location of the sector composite parameter within the population-based curve can also be scaled and separately reported to the user.

At 436, in an example, two statistical modeling analysis methods can be employed to associate and optimize sector relationship to the particularized response indication that is particular to the specified particular body anatomy, location, component, or system, wherein the particularized response indication can be indicative of disease etiology, progression, or pattern as well as severity of 'issue' or abnormality that is particular to the specified particular body anatomy, location, component, or system.

A first statistical approach can include Naïve-Bayes analysis, which can produce one or more probabilities and multiplicative factors for each sector and coefficient-parameter combination. These factors can be applied to the 78 sectors. A resultant physiology-specific composite score that can provide a physiological status indicator that is specific to a particular body anatomy location, component, or system can be produced, such as on a scale of 0 to 5 or 0 to 25 (e.g., such as for one of five major organ systems, such as Cardiovascular system, 0 to 5 or 0 to 25, Renal system, 0 to 5 or 0 to 25, Respiratory system, 0 to 5 or 0 to 25, Gastrointestinal system, 0 to 5 or 0 to 25, or Hepatic system, 0 to 5 or 0 to 25). The higher the physiology-specific score for a particular body anatomy location, component, or system, the greater the probabilistic prediction that there is an issue or abnormality with that particular body anatomy location, component, or system.

A second statistical approach that can be employed can include Logistic Regression, such as using information from a clinical knowledge base representative of a population of patients including using at least some patients other than the subject. In an example, one or more multiplicative factors can be calculated for each sector and coefficient-parameter combination. Using these probabilistic outcomes for each sector, a ranking can be created for each sector.

In an example, using information from a clinical knowledge base representative of a population of patients including using at least some patients other than the subject, such as across a population of several thousand data points these probabilities have been normalized and translated into a scoring system from 0 to 25. A score of 25 can indicate the highest probability that there is an issue or abnormality with a particular body anatomy, location, component, or system for the particular individual whose image is being analyzed.

Within a patient-specific or population-based range, such as the 0 to 25 range example, subranges can be defined, such as can respectively represent a normal response (e.g., 0 to 10), a chronic response (e.g., 11 to 16), and an emergent or acute response (e.g., 17 to 25). These subranges can be scaled to correspond to a specified cutoff value in a patient-specific or population-based distribution of such physiology-specific composite scores. For example, the 0 to 10 subrange can correspond to values within a 68% cutoff value (inclusive) on the patient-specific or population-based distribution, the subrange 11 to 16 can be scaled to correspond to values between a 69% cutoff value and a 95% cutoff value (inclusive), and the subrange 17 to 25 can be scaled to correspond to values that are greater than the 95% cutoff value. Although the above example is described using a scale from 0 to 25, another scale (e.g., 0 to 5) can be selected and used.

Trending over time (e.g., over a time period of days, weeks, months, or years) can be carried out, such as on the physiology-specific composite score, on one or more of its underlying parameters, or on the image or other at least 2D spatial or spatiotemporal response information. In an example, one or more such trends can be analyzed, such as to provide a trend-based physiological status indication or other particularized response indication that is particular to the specified particular body anatomy, location, component, or system.

Report Generation and Presentation Examples

In an example, the information generated as discussed above (e.g., one or more of the parameters, the physiology-specific composite scores, or the trends) can be presented to a diagnostician, caregiver, or other user. This can be in the form of one or more textual or pictorial reports, charts, or images that can be displayed or printed or otherwise provided to the user or to an automated process.

FIG. 5 shows an illustrative example of a report that can be presented to a user. In the example of FIG. 5, the physiology-specific composite scores can be presented to a user, such as in association with various particular body anatomy locations, components, or systems (which can be annotated "L" or "R" if separate physiologic-specific composite scores are generated from the left and right hands for that particular physiology-specific composite score). Thus, in the illustrative example of FIG. 5, the scores are presented in visual correspondence with their respective particular body anatomy location, component, or system (e.g., one or any combination of Eye (L), Eye (R), Ear/Nose/Sinus (L), Ear/Nose/Sinus (R), Jaw/Teeth (L), Jaw/Teeth (R), Cervical Spine, Thoracic Spine, Lumbar Spine, Sacrum, Coccyx/Pelvis, Nervous System, Hypothalamus, Pituitary, Pineal, Cerebral Cortex, Cerebral Vessels, Immune System, Spleen, etc.), which, in turn can be organized into more generic systems (e.g., "Sensory & Skeletal Systems," "Nervous & Immune Systems", etc.).

In an example, the physiologic specific composite scores that are presented in the user can include both "Physical" and "Autonomic" composite scores. The Physical composite scores can be determined, such as described above, from energized images that can be acquired with the dielectric barrier 103 in place. The Autonomic composite scores can be obtained, such as described above, from the energized images that can be acquired without the dielectric barrier in place. The Autonomic composite scores can include a component arising from stress or anxiety of the subject. The Physical composite scores can attenuate such a component arising from stress or anxiety of the subject.

In the example of FIG. 5, both the Physical and Autonomic composite scores can be presented in such a manner so that the user can easily tell whether they fall within a Normal range, or whether they fall outside the Normal range. Likewise, the Physical and Autonomic composite scores can be presented in such a manner so that the user can easily tell whether they were obtained using Left-hand images (L) or right-hand images (R). In the example of FIG. 5, this can be accomplished by presenting the composite scores in separate columns that can help make such distinctions, such as: Normal Physical (L), Normal Physical (R), Out of Range Physical (L), Out of Range Physical (R), Out of Range Autonomic (L), Out of Range Autonomic (R), Normal Autonomic (L), and Normal Autonomic (R). The particular composite score can be placed within the appropriate column. In the example of FIG. 5, the user's attention can be drawn toward the center-most columns to view or compare Out of Range Physical and Autonomic values.

In an example using a 0 to 25 scale, physiologic-specific composite score values in the range between 0 and 10 inclusive can be considered normal, and can be displayed without any special color, values in the range between 11 and 16 inclusive can be considered representative of chronic electrophysiology conditions or patterns, and can be displayed in a particular color (e.g., red), and values in the range between 17 and 25 inclusive can be considered representative of more emergent or acute electrophysiology conditions or patterns, and can be displayed in a particular color (e.g., red) and otherwise highlighted (e.g., with yellow highlighting background). Although the above example is described using a scale from 0 to 25, another scale (e.g., 0 to 5) can be selected and used.

In an example, a first ("Self-Scale") report such as illustrated in the example of FIG. 5 can be provided in which "Normal" and "Out of Range" can be determined with respect to a distribution or baseline of data previously obtained from the same subject, and a second ("Population Comparison") report such as illustrated in the example of FIG. 5 can be provided in which "Normal" and "Out of Range" can be determined using information from a clinical knowledge base representative of a population of patients including using at least some patients other than the subject, such as with respect to a distribution or baseline of data previously obtained from a population or subpopulation of subjects. In an example, both such Self-Scale and Population Comparison reports can be combined in a textual or pictorial report that can be displayed or otherwise presented to the user or an automated process. In an example, the user can select whether to display one or both of the individual reports or the combined report.

FIG. 6 shows another illustrative example of a report that can be presented to a user. In the example of FIG. 6, the physiology-specific composite scores can be presented in a table, such as shown. The table can be sorted, such as by organ or by side (Left-Hand, Right-Hand) for both the Physical System measurements (e.g., determined using energized images obtained without the capacitive barrier) and the Autonomic System measurements (e.g., determined using energized images obtained with the capacitive barrier). In an example, the table presented can be user-filtered, such as by one or more organs, by Autonomic or Physical, or by or one or more other user-specified display filter characteristics (e.g., such as low-to-high or high-to-low physiology-specific composite score).

In the examples shown in FIGS. 5-6, or other examples, textual or other explanatory content can also be provided, such as can help the user understand relationships between organ system results, between Physical and Autonomic results, between Left-Hand and Right-Hand results, or to assist user-interpretation in any other way. For example, it is believed that the physiology-specific composite scores of certain particular body anatomy locations, components, or systems interact with other physiology-specific composite scores. In another example, it is also believed that a greater difference between Left-Hand and Right-Hand physiologic-specific composite scores for a particular body anatomy location, component, or system, (or set of such physiology-specific composite scores) can correlate to a greater likelihood of the presence of a corresponding pathological physiological status.

In an example, the information displayed or otherwise presented to the user need not focus on the physiologic-specific composite scores, but can additionally or alternatively include information about one or more parameters, which can optionally be presented together with information about one or more corresponding particular body anatomy locations, components, or systems, or any helpful explanatory test. In an illustrative example, this can include information about the Reference-Subjective or Reference-Objective parameters described above, or differences between the Reference-Subjective or Reference-Objective parameters, or one or more trends in any of these, such as together with an interpretive explanation of how such information can be influenced by nervous system issues of the subject.

Calibration Examples

In an example, the system described herein can be calibrated for acquiring the energized images as described above. In an example, this calibration can be carried out as explained below, such as on the same day on which the actual energized images are to be acquired from the subject.

First, a series of ten energized finger images can be acquired, using a specified manufacture of calibration probe rather than a human finger and then matrix analysis can be performed. Each image can be represented by an intensity matrix having two spatial dimensions (e.g., x=320 pixels by y=240 pixels) and an intensity dimension.

Then, the image data can be processed, such as to determine a variability in intensity and geographical location (finger position). Each of the ten images can be centered with respect to a calibration template image, and then compared against the calibration template image. A respective measure of the difference between the intensity and geographical location of the image and the calibration image can be determined.

In an example, the calibration template image can be a calculated composite matrix that can be determined based on calibration images gathered over time from several different cameras and assessed for variability, such as across hundreds of images. In an example, the calibration template image can be established by generating a representative radial profile of 5 degrees from the various calibration images gathered over time, and the representative radial profile can be copied 72 times at 5 degree increments to form a 360 degree calibration template image.

In an example, the calibration template image can be a calculated composite matrix that can be determined based on one or more calibration images gathered using a calibration probe of a specified manufacture, such as a specified size, shape, or material (e.g., a tungsten-composite solid cylindrical metal probe). The calibration probe can be placed directly onto the glass electrode, and one or more images can be obtained. In an example, 5 images can be captured, but not recorded, and the following 10 images are captured and recorded. The 10 recorded images of the calibration probe can be analyzed as follows.

First, the background noise can be determined, such as by finding the highest intensity gradient in the calibration probe image (e.g., the inner edge of the calibration probe image). Then, the lower intensity pixels can be removed until the radius vector is consistent to the inner edge (highest intensity gradient). This radius vector can be calculated as the number of pixels from the center of the image to the inner edge of the calibration probe, as represented by the highest intensity gradient.

Next, from the center of the calibration probe image, rings generated using specified multiples of the length of the inner edge radius vector can be calculated (e.g., 1.2·* length of radius vector, 1.4·* length of radius vector, 1.8·* length of radius vector, etc.). Such rings can be equally-spaced. Within each such ring, the area and average intensity can be calculated, such as described above with reference to similar parameter calculations. The consistency of the area and average intensity for each ring can be analyzed across all 10 recorded calibration probe images, and a range of +/−one standard deviation can be calculated. If the standard deviation falls within a specified range, then an acceptable level of calibration can be declared to exist, and acquisition and processing of actual energized fingertip images can commence. Otherwise, an unacceptable level of calibration can be declared to exist, and either: (1) acquisition and processing of actual energized fingertip images can be inhibited, prevented, or qualified, or (2) one or more data acquisition or signal processing parameters can be adjusted and used.

Dynamic Imaging Examples

The apparatuses and methods described herein can include using not only static image capture and analysis (or other static at least 2D spatial response capture or analysis), but can additionally or alternatively include using dynamic image capture and analysis, such as at least two (spatial) dimensional spatiotemporal response capture or analysis). In an illustrative example, a static image capture process can include capturing images for an exposure period of 0.5 seconds, during which 10 frames per second can be captured, thereby capturing 5 static image frames during the 0.5 second exposure period, after an initial specified ramp-up delay, such as can be established by hardware, software, or firmware. In an illustrative example, a dynamic image capture process can include capturing images for an exposure period that can be between 0.5 seconds and 30 seconds, such as using a 10 frame per second image capture rate, after an initial 200 millisecond delay, such as can be established by hardware, software, or firmware. This can result in capturing close to 300 image frames during a 30 second exposure period.

In an example, dynamic image or spatiotemporal response analysis can include computing the parameters and coefficients (such as described above) for each image frame in the dynamic imaging set of images, and optionally performing Fourier or harmonic analysis to assess the frequency response of one or more such coefficients and parameters. Such frequency domain information can be used in the determination of the physiological status indication or other particularized response indication that is particular to the specified particular body anatomy, location, component, or system, such as by statistical comparison to the within-patient distribution or to the population-based distribution. It is believed that such frequency domain information may further improve the sensitivity or specificity of the physiological status indication or other particularized response indication that is particular to the specified particular body anatomy, location, component, or system.

It is believed that each parameter can provide a unique frequency measure that can be calculated, specific to each person and each organ system for this person, a composite profile of which may be able yield profile information of individuals, such as for later recognition or identification of the subject using the system. The frequency measure of individual parameters, coefficients, or of the composite profile, can be used to provide a baseline measure, to which comparison can be made to determine a physiological status of the subject.

Additional Notes & Examples

Example 1 can include subject matter (such as an apparatus, a method, a means for performing acts, or a storage device or other tangible nontransitory device-readable medium including instructions that, when performed by the device, cause the device to perform acts) that can include or use obtaining at least two (spatial) dimensional (2D) spatial or spatiotemporal response information (such as an image, a time-series of images, or frequency domain or time-frequency information derived from images or other response information) of visible or other light (e.g., in the electromagnetic spectrum between the visible spectrum and UV spectrum, inclusive) associated with a body part, such as around a finger or toe of a subject. The spatial response information can be obtained at a light detector capable of providing information about at least first and second spatial dimensions that are orthogonal to each other, and can optionally include a temporal or frequency dimension. The light can be obtained in response to electromagnetic field (e.g., electrical) stimulation of the finger or toe sufficient to produce the light at the light detector around the finger or toe.

The spatial response information can be mapped, registered, or otherwise associated to a specified particular body anatomy, location, component, or system (e.g., that is particular to a selected particular one of: a cardiovascular system, a gastrointestinal/endocrine system, a respiratory system, a renal system, or a hepatic system) that is remote from the finger or toe at which the image information was obtained. The associating can include radially sectoring the at least 2D spatial response information—which can be included in at least two spatial dimensional spatiotemporal response information, such as a time series of images, for example. A plurality of parameters can be computed (e.g., Center Point, Minimum Radius, Maxim Radius, Image Angle, Background Noise Level, Inner Radius, Area, Intensity, Form-One, Form-Two, Entropy, Fractal, Reference-Subjective, or Break). Computing parameters can include using the radially sectored 2D spatial response information to compute at least one of the parameters (e.g., Area, Intensity, Form-One, Form-Two, Entropy, Fractal, Reference-Subjective, or Break), which can be computed for a particular radial sector (or a specified subset of the radial sectors that is smaller than the set of all radial sectors).

At least one of the parameters can be adjusted (e.g., scaled, normalized, discarded) or compared (e.g., to a corresponding threshold value, or to a population or subpopulation distribution of values) using information from a clinical knowledge base (e.g., stored in a memory circuit, a database, or obtained) representative of a population of patients including using at least some patients other than the subject (e.g., in addition or as an alternative to information obtained from the same subject).

The at least one adjusted parameter can be used for using the spatial response information for providing a particularized response indication (e.g., a odds ratio or other form of physiological status indicator) that is particular to the specified particular body anatomy, location, component, or system.

Example 2 can include or use, or can optionally be combined with the subject matter of Example 1 to optionally include or use, the particularized response indication indicating a relative risk (e.g., using an odds ratio or other indication) of an abnormal physiological state of the specified particular body anatomy, location, component, or system relative to at least one of (1) at least one other particular body anatomy, location, component, or system or (2) a normal physiological state of the specified particular body anatomy, location, component, or system.

Example 3 can include or use, or can optionally be combined with the subject matter of any of Examples 1 or 2 to optionally include or use, the at least 2D spatial response information being pre-processed, e.g., before computing the plurality of parameters, such as to attenuate or ignore one or more spatial response artifacts within at least one designated area of the at least 2D spatial response information (e.g., within an ellipse or other area corresponding to the outline of the fingertip).

Example 4 can include or use, or can optionally be combined with the subject matter of any of Examples 1 through 3 to optionally include or use, the signal processor circuit being configured such that the at least 2D spatial response information can be pre-processed, e.g., before computing the plurality of parameters, such as to automatically orient the at least 2D spatial response information at least one of rotationally or translationally. This can include using the live image to orient the energized image to within a few degrees, as explained above.

Example 5 can include or use, or can optionally be combined with the subject matter of any of Examples 1 through 4 to optionally include or use, the at least 2D spatial response information being pre-processed, e.g., before computing the plurality of parameters, such as to calibrate the at least 2D spatial response information. Such calibration can include using calibration at least 2D spatial response information obtained using a specified manufacture (e.g., size, shape, material) of calibration probe (e.g., a solid cylindrical tungsten or other metal calibration probed) in place of the finger or toe of the subject.

Example 6 can include or use, or can optionally be combined with the subject matter of any of Examples 1 through 5 to optionally include or use, the calibration at least 2D spatial response information to normalize the at least 2D spatial response information across different light detectors. This can help reduce or eliminate variability between measurements made with different apparatuses such as described herein.

Example 7 can include or use, or can optionally be combined with the subject matter of any of Examples 1 through 6 to optionally include or use, the calibration at least 2D spatial response information to adjust at least one of the parameters.

Example 8 can include or use, or can optionally be combined with the subject matter of any of Examples 1 through 6 to optionally include or use, the calibration at least 2D spatial response information for qualifying whether the at least 2D spatial response information is suitable for use for computing at least one of the parameters.

Example 9 can include or use, or can optionally be combined with the subject matter of any of Examples 1 through 7 to optionally include or use, the particularized response indication being exclusive to the specified particular body anatomy, location, component, or system, and being exclusive of other particular body anatomy, locations, components, or systems.

Example 10 can include or use, or can optionally be combined with the subject matter of any of Examples 1 through 9 to optionally include or use, the associating including computing the particularized response indication using both at least 2D spatial light intensity aggregate and density information.

Example 11 can include or use, or can optionally be combined with the subject matter of any of Examples 1 through 10 to optionally include or use, an electrode that can be configured to provide the electromagnetic field or electrical stimulation to the finger or toe of the subject. The stimulation can include AC electrical stimulation. The electrode can be transparent enough to pass at least a portion of the visible or other light around the finger or toe of a subject. The light detector can be included in the apparatus. The light detector can be configured to receive from the electrode the passed at least a portion of the visible or other light around the finger or toe of a subject. The light detector can be configured to provide to the signal processor circuit at least two-dimensional (2D) spatial response information of visible or other light around a finger or toe of a subject. A dielectric barrier can be provided, such as between (1) the finger or toe of the subject and (2) the electrode or the light detector. The dielectric barrier can be configured to be transparent enough to pass at least a portion of the visible or other light around the finger or toe of the subject. The particularized response indication can be exclusive to the specified particular body anatomy, location, component, or system, and can be exclusive of other particular body anatomy, locations, components, or systems. The associating can include computing the particularized response indication using both at least 2D spatial light intensity aggregate and density information. The spatial response information can include at least 2D first spatial response information and at least 2D second spatial response information. The associating can include computing the particularized response information using differential or other relative information that can be determined between (1) the at least 2D first spatial response information, obtained with the presence of a dielectric barrier between the finger or toe and the light detector, and (2) the at least 2D second spatial response information, obtained without the presence of the dielectric barrier between the finger or toe and the light detector.

Example 12 can include or use, or can optionally be combined with the subject matter of any of Examples 1 through 11 to optionally include or use, the spatial response information including at least 2D first spatial response information and at least 2D second spatial response information. The associating can include computing the particularized response information using differential or other relative information determined between (1) the at least 2D first spatial response information, obtained with the presence of a dielectric barrier between the finger or toe and the light detector, and (2) the at least 2D second spatial response information, obtained without the presence of the dielectric barrier between the finger or toe and the light detector.

Example 13 can include or use, or can optionally be combined with the subject matter of any of Examples 1 through 12 to optionally include or use the associating including computing the particularized response indication using a trending over time of each of the spatial light intensity aggregate information and the spatial light intensity density information.

Example 14 can include or use, or can optionally be combined with the subject matter of any of Examples 1 through 13 to optionally include or use the associating including computing the particularized response indication using a polynomial relationship of an area and an average intensity of the spatial light intensity information.

Example 15 can include or use, or can optionally be combined with the subject matter of any of Examples 1 through 14 to optionally include or use, determining a physiological status indicator (e.g., an odds ratio indicating a relative likelihood of an abnormal physiological state) using the particularized response information. The physiological status indicator can be provided to a user or automated process.

Example 16 can include or use, or can optionally be combined with the subject matter of any of Examples 1 through 15 to optionally include or use the spatial response information for providing a particularized response indication that is particular to the specified particular body anatomy location, component, or system comprising a selected particular one of: a cardiovascular system, a gastrointestinal/endocrine system, a respiratory system, a renal system, or a hepatic system.

Example 17 can include or use, or can optionally be combined with the subject matter of any of Examples 1 through 16 to optionally include or use, the spatial response information for providing a particularized response indication including determining an Entropy parameter of the spatial response information.

Example 18 can include or use, or can optionally be combined with the subject matter of any of Examples 1 through 17 to optionally include or use, the spatial response information for providing a particularized response indication including determining a Form-One parameter of the spatial response information that is within a specified centered first annulus region between an inner first radius of the annulus and an outer second radius of the annulus.

Example 19 can include or use, or can optionally be combined with the subject matter of any of Examples 1 through 18 to optionally include or use, the spatial response information for providing the particularized response indication including also determining a Form-Two parameter of the spatial response information that is within a specified centered second annulus region between the inner first radius of the annulus and an outer third radius of the annulus, wherein the third radius exceeds the second radius.

Example 20 can include or use, or can optionally be combined with the subject matter of any of Examples 1 through 19 to optionally include or use, the spatial response information for providing the particularized response indication includes determining a Fractal parameter of the spatial response information using (1) a perimeter of spatial response pixels exceeding a specified threshold value and (2) a spatial variation in the perimeter of spatial response pixels exceeding the specified threshold value.

Example 21 can include or use, or can optionally be combined with the subject matter of any of Examples 1 through 20 to optionally include or use, the spatial response information including an at least 2D first spatial response information and an at least 2D second spatial response information, and wherein the translating the spatial response information into a particularized response indication includes using first differential information determined between (1) the first spatial response, obtained with the presence of a dielectric barrier between the finger or toe and the light detector; and (2) the second image, obtained without the presence of the dielectric barrier between the finger or toe and the light detector; and wherein the spatial response includes an at least 2D third spatial response and an at least 2D fourth spatial response, and wherein the translating the spatial response information into a particularized response indication includes using second differential information determined between (1) the third spatial response, obtained as a calibration spatial response with the presence of a dielectric barrier between the finger or toe and the light detector; and (2) the fourth spatial response, obtained as a calibration image without the presence of the dielectric barrier between the finger or toe and the light detector.

Example 22 can include or use, or can optionally be combined with the subject matter of any of Examples 1 through 21 to optionally include or use, the second spatial response, the third spatial response, and the fourth spatial response being obtained from the same subject and same day calibration spatial response.

Example 23 can include or use, or can optionally be combined with the subject matter of any of Examples 1 through 22 to optionally include or use, the first spatial response and the second spatial response being obtained from the same subject, and wherein the third spatial response and the fourth spatial response are obtained by composite information from different subjects.

Example 24 can include or use, or can optionally be combined with the subject matter of any of Examples 1 through 23 to optionally include or use, the spatial response including a first spatial response and a second spatial response, and wherein the translating the spatial response information into a particularized response indication includes computing the particularized response indication using a Reference-Subjective parameter determined from (1) a composite intensity and (2) a spatial extent of active pixels, as determined for each of (1) the first spatial response, obtained with the presence of a dielectric barrier between the finger or toe and the light detector; and (2) the second spatial response, obtained without the presence of the dielectric barrier between the finger or toe and the light detector.

Example 25 can include or use, or can optionally be combined with the subject matter of any of Examples 1 through 19 to optionally include or use, the spatial response information for providing a particularized response indication includes computing the physiological status indicator using an Reference-Subjective parameter determined from (1) a composite intensity and (2) a spatial extent of active pixels.

Example 26 can include or use, or can optionally be combined with the subject matter of any of Examples 1 through 25 to optionally include or use, sampling the spatial response information repeatedly over sampling period of interest at a sampling rate exceeding twice a frequency bandwidth of a parameter of interest; determining a frequency characteristic of the parameter of interest; and determining the physiological status indication using the frequency characteristic of the parameter of interest.

Example 27 can include or use, or can optionally be combined with the subject matter of any of Examples 1 through 26 to optionally include or use, displaying a visual illustration of the subject; and labeling the specified particular body anatomy, location, component, or system with information about the particularized response indicator that is particular to the specified particular body anatomy, location, component, or system.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The scope of the invention should be determined with reference to the appended claims, along with the full scope of equivalents to which such claims are entitled.

The claimed invention is:

1. An apparatus comprising:
 a signal processor circuit, configured to:
  obtain at least two-dimensional spatial response information of visible or other light around a finger or toe of a subject, the spatial response information obtained at a light detector configured to provide information regarding at least first and second spatial dimensions that are orthogonal to each other, the light obtained in response to electrical stimulation of the finger or toe sufficient to produce the light around the finger or toe; and
  associate the spatial response information to a specified particular body anatomy, location, component, or system that is remote from the finger or toe at which the spatial response information was obtained, the associating including:
   radially sectoring the at least two-dimensional spatial response information;
   computing a plurality of parameters, including using the radially sectored at least two-dimensional spatial response information to compute at least one of the parameters;
   adjusting or comparing at least one of the parameters using information from a clinical knowledge base representative of a population of patients including using at least some patients other than the subject; and
   using the at least one adjusted parameter for using the spatial response information for providing a particularized response indication that is particular to the specified particular body anatomy, location, component, or system;
 an electrode, configured to provide the electrical stimulation to the finger or toe; wherein
  the electrical stimulation includes AC electrical stimulation, the electrode is transparent enough to pass at least a portion of the visible or other light around the finger or toe;
  the light detector is configured to receive through the electrode the passed portion of the visible or other light around the finger or toe; and
  the light detector is configured to provide to the signal processor circuit th two-dimensional spatial response information of visible or other light around the finger or toe; and
 a removable dielectric barrier, between (1) the finger or toe of the subject and (2) the electrode, wherein the dielectric barrier is configured to be transparent enough to pass the portion of the visible or other light around the finger or toe;
  wherein the particularized response indication is exclusive to the specified particular body anatomy, location, component, or system, and is exclusive of other particular body anatomy, locations, components, or systems;
  wherein the associating further includes computing the particularized response indication using both at least two-dimensional spatial light intensity aggregate and density information; and
  wherein the spatial response information includes a first at least two-dimensional spatial response information and a second at least two-dimensional spatial response information, and wherein the associating includes computing the particularized response indication using differential or other relative information determined between (1) the first spatial response information, obtained with the presence of a dielectric barrier between the finger or toe and the electrode; and (2) the second spatial response information, obtained without the presence of the dielectric barrier after the dielectric barrier is removed from between the finger or toe and the electrode.

2. An apparatus comprising:
 a signal processor circuit, configured to:
  obtain at least two-dimensional spatial response information of visible or other light around a finger or toe of a subject, the spatial response information obtained at a light detector configured to provide information regarding at least first and second spatial dimensions that are orthogonal to each other, the light obtained in response to electrical stimulation of the finger or toe sufficient to produce the light around the finger or toe; and
  associate the spatial response information to a specified particular body anatomy, location, component, or system that is remote from the finger or toe at which the spatial response information was obtained, the associating including:
  radially sectoring the at least two-dimensional spatial response information;
  computing a plurality of parameters, including using the radially sectored at least two dimensional spatial response information to compute at least one of the parameters;
  adjusting or comparing at least one of the parameters using information from a clinical knowledge base representative of a population of patients including using at least some patients other than the subject; and
  using the at least one adjusted parameter for using the spatial response information for providing a particularized response indication that is particular to the specified particular body anatomy, location, component, or system;
wherein the spatial response information includes a first at least two-dimensional spatial response information and a second at least two-dimensional spatial response information, and wherein the signal processor circuit is configured to use the spatial response information for providing a particularized response indication including using first differential information determined between (1) the first spatial response information, obtained with the presence of a removable dielectric barrier between the finger or toe and the electrode; and (2) the second spatial response information, obtained without the presence of the dielectric barrier after the dielectric barrier is removed from between the finger or toe and the electrode; and
wherein the spatial response information further includes a third at least two-dimensional spatial response information and a fourth at least two-dimensional spatial response, and wherein the signal processor circuit is configured to use the spatial response information for providing a particularized response indication further including using second differential information determined between (1) the third spatial response information, obtained as a calibration spatial response with the presence of a dielectric barrier between the finger or toe and the electrode; and
(2) the fourth spatial response information, obtained as a calibration image without the presence of the dielectric barrier between the finger or toe and the electrode.

3. The apparatus of claim 2, wherein the first spatial response, the second spatial response, the third spatial response, and the fourth spatial response are obtained from the same subject and same day calibration spatial response.

4. The apparatus of claim 2, wherein the first spatial response and the second spatial response are obtained from the same subject, and wherein the third spatial response and the fourth spatial response are obtained by composite information from different subjects.

5. An apparatus comprising:
a signal processor circuit, configured to:
  obtain at least two-dimensional spatial response information of visible or other light around a finger or toe of a subject, the spatial response information obtained at a light detector configured to provide information regarding at least first and second spatial dimensions that are orthogonal to each other, the light obtained in response to electrical stimulation of the finger or toe sufficient to produce the light around the finger or toe; and
  associate the spatial response information to a specified particular body anatomy, location, component, or system that is remote from the finger or toe at which the spatial response information was obtained, the associating including:
    radially sectoring the at least two-dimensional spatial response information;
    computing a plurality of parameters, including using the radially sectored at least two-dimensional spatial response information to compute at least one of the parameters;
    adjusting or comparing at least one of the parameters using information from a clinical knowledge base representative of a population of patients including using at least some patients other than the subject; and
    using the at least one adjusted parameter for using the spatial response information for providing a particularized response indication that is particular to the specified particular body anatomy, location, component, or system;
wherein the spatial response information includes a first spatial response information and a second spatial response information, and wherein the signal processor circuit is configured to use the spatial response information for providing a particularized response indication including computing the particularized response indication using a Reference-Subjective parameter determined from (1) an average intensity of a sector of an image (2) an average intensity of a sector of a calibration image and (3) a spatial extent of active pixels, as determined for each of (1) the first spatial response information, obtained with the presence of a removable dielectric barrier between the finger or toe and the electrode; and (2) the second spatial response information, obtained without the presence of the dielectric barrier after the dielectric barrier is removed from between the finger or toe and the electrode.

6. An apparatus comprising:
a signal processor circuit, configured to:
  obtain at least two-dimensional spatial response information of visible or other light around a finger or toe of a subject, the spatial response information obtained at a light detector configured to provide information regarding at least first and second spatial dimensions that are orthogonal to each other, the light obtained in response to electrical stimulation of the finger or toe sufficient to produce the light around the finger or toe; and
  associate the spatial response information to a specified particular body anatomy, location, component, or system that is remote from the finger or toe at which the spatial response information was obtained, the associating including:
    radially sectoring the at least two-dimensional spatial response information;
    computing a plurality of parameters, including using the radially sectored at least two-dimensional spatial response information to compute at least one of the parameters;
      adjusting or comparing at least one of the parameters using information from a clinical knowledge base representative of a population of patients including using at least some patients other than the subject; and
      using the at least one adjusted parameter for using the spatial response information for providing a particularized response indication that is particular to the specified particular body anatomy, location, component, or system;

wherein the signal processor circuit is configured to use the spatial response information for providing a particularized response indication including computing the physiological status indicator using a Reference-Subjective parameter determined from (1) an average intensity of a sector of an image and (2) an average intensity of a sector of a calibration image and (3) a spatial extent of active pixels wherein the spatial response information includes a first at least two-dimensional spatial response information and a second at least two-dimensional spatial response information, and wherein the signal processor circuit is configured to use the spatial response information for providing a particularized response indication including using first differential information determined between (1) the first spatial response information, obtained with the presence of a removable dielectric barrier between the finger or toe and the electrode; and (2) the second spatial response information, obtained without the presence of the dielectric barrier after the dielectric barrier is removed from between the finger or toe and the electrode.

7. An apparatus comprising:
a signal processor circuit, configured to:
  obtain at least two-dimensional spatial response information of visible or other light around a finger or toe of a subject, the spatial response information obtained at a light detector configured to provide information regarding at least first and second spatial dimensions that are orthogonal to each other, the light obtained in response to electrical stimulation of the finger or toe sufficient to produce the light around the finger or toe; and
  associate the spatial response information to a specified particular body anatomy, location, component, or system that is remote from the finger or toe at which the spatial response information was obtained, the associating including:
    radially sectoring the at least two-dimensional spatial response information;
    computing a plurality of parameters, including using the radially sectored at least two-dimensional spatial response information to compute at least one of the parameters;
    adjusting or comparing at least one of the parameters using information from a clinical knowledge base representative of a population of patients including using at least some patients other than the subject; and
    using the at least one adjusted parameter for using the spatial response information for providing a particularized response indication that is particular to the specified particular body anatomy, location, component, or system;
  wherein the signal processor circuit is configured to:
    sample the spatial response information repeatedly over a sampling period of interest at a sampling rate exceeding twice a frequency bandwidth of a parameter of interest;
    determine a frequency characteristic of the parameter of interest; and
    determine a physiological status indication using the frequency characteristic of the parameter of interest wherein the spatial response information includes a first at least two-dimensional spatial response information and a second at least two-dimensional spatial response information, and wherein the signal processor circuit is configured to use the spatial response information for providing a particularized response indication including using first differential information determined between (1) the first spatial response information, obtained with the presence of a removable dielectric barrier between the finger or toe and the electrode; and (2) the second spatial response information, obtained without the presence of the dielectric barrier after the dielectric barrier is removed from between the finger or toe and the electrode.

8. The apparatus of any one of claim 1, 2, 5, 6, or 7, wherein the signal processor circuit is configured such that the particularized response indication indicates a relative risk of an abnormal physiological state of the specified particular body anatomy, location, component, or system relative to at least one of (1) at least one other particular body anatomy, location, component, or system or (2) a normal physiological state of the specified particular body anatomy, location, component, or system.

9. The apparatus of any one of claim 1, 2, 5, 6, or 7, wherein the signal processor circuit is configured such that the at least two-dimensional spatial response information is pre-processed, before computing the plurality of parameters, to attenuate or ignore one or more spatial response artifacts within at least one designated area of the at least two-dimensional spatial response information.

10. The apparatus of any one of claim 1, 2, 5, 6, or 7, wherein the signal processor circuit is configured such that the at least two-dimensional spatial response information is pre-processed, before computing the plurality of parameters, to automatically orient the at least two-dimensional spatial response information at least one of rotationally or translationally.

11. The apparatus of any one of claim 1, 2, 5, 6, or 7, wherein the signal processor circuit is configured to determine the particularized response indication including trending over time both at least two-dimensional spatial light intensity aggregate and density information.

12. The apparatus of any one of claim 1, 2, 5, 6, or 7, wherein the signal processor circuit is configured to determine the particularized response indication using a polynomial relationship of an area and an average intensity of spatial light intensity information.

13. The apparatus of any one of claim 1, 2, 5, 6, or 7, wherein the signal processor circuit is configured to:
  determine a physiological status indicator using the particularized response information; and
  provide the physiological status indicator to a user or automated process.

14. The apparatus of any one of claim 1, 2, 5, 6, or 7, wherein the signal processor circuit is configured to use the spatial response information for providing a particularized response indication that is particular to a selected particular one of: a cardiovascular system, a gastrointestinal/endocrine system, a respiratory system, a renal system, or a hepatic system.

15. The apparatus of any one of claim 1, 2, 5, 6, or 7, wherein the signal processor circuit is configured to use the spatial response information for providing a physiological status indicator that is particular to a selected particular one of: a cardiovascular system, a gastrointestinal/endocrine system, a respiratory system, a renal system, or a hepatic system.

16. The apparatus of any one of claim 1, 2, 5, 6, or 7, wherein the signal processor circuit is configured to use the spatial response information for providing a particularized response indication including using a determining of an Entropy parameter of the spatial response information.

17. The apparatus of any one of claim 1, 2, 5, 6, or 7, wherein the signal processor circuit is configured to use the spatial response information for providing a particularized response indication including determining a Form-One parameter of the spatial response information that is within a specified centered first annulus region between an inner first radius of the annulus and an outer second radius of the annulus, wherein the Form-One parameter is calculated using a ratio of the perimeter length of the region and pixel intensity within the region above a background noise level.

18. The apparatus of any one of claim 1, 2, 5, 6, or 7, wherein the signal processor circuit is configured to use the spatial response information for providing a particularized response indication including determining a Form-One parameter of the spatial response information that is within a specified centered first annulus region between an inner first radius of the annulus and an outer second radius of the annulus, wherein the Form-One parameter is calculated using a ratio of the perimeter length of the region and pixel intensity within the region above a background noise level; and the signal processor circuit is configured to use the spatial response information for providing the particularized response indication including also determining a Form-Two parameter of the spatial response information that is within a specified centered second annulus region between the inner first radius of the annulus and an outer third radius of the annulus, wherein the third radius exceeds the second radius, wherein the Form-Two parameter is calculated using a ratio of the perimeter length of the second region and pixel intensity within the second region above a background noise level.

19. The apparatus of any one of claim 1, 2, 5, 6, or 7, wherein the signal processor circuit is configured to use the spatial response information for providing the particularized response indication including determining a Fractal parameter of the spatial response information using (1) a perimeter of spatial response pixels exceeding a specified threshold value and (2) a spatial variation in the perimeter of spatial response pixels exceeding the specified threshold value.

20. The apparatus of any one of claim 1, 2, 5, 6, or 7, further comprising:
a display, configured to display a visual illustration of the subject; and
wherein the display is configured to label a displayed indication of the specified particular body anatomy, location, component, or system with information about the particularized response indicator that is particular to the specified particular body anatomy, location, component, or system.

21. The apparatus of any of claim 1, 2, 6, or 7 wherein the spatial response information includes a first spatial response information and a second spatial response information, and wherein the signal processor circuit is configured to use the spatial response information for providing a particularized response indication including computing the particularized response indication using a Reference-Subjective parameter determined from (1) an average intensity of a sector of an image (2) an average intensity of a sector of a calibration image and (3) a spatial extent of active pixels, as determined for each of (1) the first spatial response information, obtained with the presence of a removable dielectric barrier between the finger or toe and the electrode; and (2) the second spatial response information, obtained without the presence of the dielectric barrier after the dielectric barrier is removed from between the finger or toe and the electrode.

22. The apparatus of any of claim 1, 2, or 7 wherein the signal processor circuit is configured to use the spatial response information for providing a particularized response indication including computing the physiological status indicator using a Reference-Subjective parameter determined from (1) an average intensity of a sector of an image (2) an average intensity of a sector of a calibration image and (3) a spatial extent of active pixels.

23. The apparatus of any of claim 1, or 2 wherein the signal processor circuit is configured to:
sample the spatial response information repeatedly over sampling period of interest at a sampling rate exceeding twice a frequency bandwidth of a parameter of interest;
determine a frequency characteristic of the parameter of interest; and
determine a physiological status indication using the frequency characteristic of the parameter of interest.

* * * * *